United States Patent
Oberdorff et al.

(10) Patent No.: US 11,672,882 B1
(45) Date of Patent: Jun. 13, 2023

(54) AIR TREATMENT SYSTEM FOR VEHICLES

(71) Applicant: ProAir, LLC, Haslet, TX (US)

(72) Inventors: David Oberdorff, Elizabethtown, PA (US); Homauon Noroozi, Rockford, MI (US); James R Schreiber, Dover, PA (US); Reed D Hooks, Peoria, AZ (US); Dean G Wertz, York, PA (US); Duane L Hyson, Stewartstown, PA (US); Jerry E Miller, Azle, TX (US); Charles W McAllister, II, Haslet, TX (US); Calvin J Herman, Dover, PA (US)

( * ) Notice: Subject to any disclaimer, the term of this patent is extended or adjusted under 35 U.S.C. 154(b) by 0 days.

(21) Appl. No.: 17/352,341

(22) Filed: Jun. 20, 2021

Related U.S. Application Data

(60) Provisional application No. 63/041,999, filed on Jun. 21, 2020.

(51) Int. Cl.
```
B01D 46/00     (2022.01)
A61L 9/20      (2006.01)
B60H 1/00      (2006.01)
B60H 3/06      (2006.01)
B60H 3/00      (2006.01)
B01D 46/62     (2022.01)
```

(52) U.S. Cl.
CPC ............ *A61L 9/20* (2013.01); *B01D 46/0005* (2013.01); *B01D 46/0027* (2013.01); *B01D 46/62* (2022.01); *B60H 1/00371* (2013.01); *B60H 3/0078* (2013.01); *B60H 3/0608* (2013.01); *A61L 2209/14* (2013.01); *A61L 2209/16* (2013.01)

(58) Field of Classification Search
CPC . B01D 46/0005; B01D 46/0027; B01D 46/62
See application file for complete search history.

(56) References Cited

U.S. PATENT DOCUMENTS

| | | | |
|---|---|---|---|
| 4,210,429 A | 7/1980 | Golstein | |
| 4,694,179 A | 9/1987 | Lew et al. | |
| 4,869,734 A | 9/1989 | Jacquish | |
| 5,330,722 A | 7/1994 | Pick et al. | |
| 5,656,242 A | 8/1997 | Morrow et al. | |
| 5,690,550 A * | 11/1997 | Mikowski | B60H 1/345 454/155 |
| 5,891,399 A | 4/1999 | Owesen | |

(Continued)

FOREIGN PATENT DOCUMENTS

| CN | 209263206 U | * | 8/2019 |
|---|---|---|---|
| JP | S60250503 A | * | 12/1985 |

(Continued)

*Primary Examiner* — Robert A Hopkins
(74) *Attorney, Agent, or Firm* — Peter Materna

(57) ABSTRACT

An air treatment system may create an air flow pattern in a vehicle interior space, using air discharges in multiple directions and louvers such that some vanes within a louver are not parallel to other vanes within the louver. An air treatment system may provide bulk air flow to the vehicle interior and directed airflow to a driver region. An air flow system may comprise, internally, a constriction bounded by an edge of a UV light shield and an edge of a filter housing. Such air treatment systems, using filtration and UV light, effectively remove or kill viruses and other pathogens, for use in buses and similar vehicles.

7 Claims, 28 Drawing Sheets

(56) References Cited

U.S. PATENT DOCUMENTS

| | | |
|---|---|---|
| 6,464,760 B1 | 10/2002 | Sham et al. |
| 6,494,940 B1 | 12/2002 | Hak |
| 6,497,840 B1 | 12/2002 | Palestro et al. |
| 6,579,336 B1 | 6/2003 | Duffy et al. |
| 6,613,277 B1 | 9/2003 | Monagan |
| 6,718,787 B1 | 4/2004 | Hille et al. |
| 6,773,477 B2 | 8/2004 | Lindsay |
| 6,787,782 B1 | 9/2004 | Krosney et al. |
| 6,796,132 B1 | 9/2004 | Hille et al. |
| 6,797,042 B2 | 9/2004 | LaFerriere et al. |
| 6,805,733 B2 | 10/2004 | Engel et al. |
| 6,855,295 B2 | 2/2005 | Kulp |
| 6,984,259 B2 | 1/2006 | Hurst |
| 6,991,532 B2 | 1/2006 | Goldsmith |
| 7,051,544 B2 | 5/2006 | Hille et al. |
| 7,074,250 B1 | 7/2006 | Chipner et al. |
| 7,326,387 B2 | 2/2008 | Arts et al. |
| 7,407,633 B2 | 8/2008 | Potember et al. |
| 7,588,614 B2 | 9/2009 | Morse et al. |
| 7,632,340 B2 | 12/2009 | Brady et al. |
| 7,837,933 B2 | 11/2010 | Sevack et al. |
| 7,931,726 B2 | 4/2011 | Karlsson et al. |
| 7,938,927 B2 | 5/2011 | Sundvik et al. |
| 7,947,101 B2 | 5/2011 | Devine et al. |
| 7,976,195 B2 | 7/2011 | Engel et al. |
| 8,226,899 B2 | 7/2012 | Woodbridge |
| 8,318,084 B2 | 11/2012 | Johnson et al. |
| 8,506,367 B2 | 8/2013 | Cermak et al. |
| 8,540,791 B2 | 9/2013 | Morgan |
| 8,545,753 B2 | 10/2013 | Sevack et al. |
| 8,747,753 B2 | 6/2014 | Engel et al. |
| 8,779,385 B2 | 7/2014 | Noori |
| 9,157,642 B2 | 10/2015 | Maeng et al. |
| 9,327,047 B1 | 5/2016 | Lichtblau |
| 9,393,338 B2 | 7/2016 | Livchak et al. |
| 9,480,768 B2 | 11/2016 | Krosney et al. |
| 9,603,956 B2 | 3/2017 | Newham |
| 9,956,306 B2 | 5/2018 | Brais et al. |
| 9,974,880 B2 | 5/2018 | Krosney |
| 9,993,571 B2 | 6/2018 | Lin et al. |
| 10,322,204 B2 | 6/2019 | He |
| 10,639,575 B2 | 5/2020 | Morgan et al. |
| 11,000,622 B2 | 5/2021 | Krosney |
| 2004/0013583 A1 | 1/2004 | Burkhardt |
| 2004/0086422 A1 | 5/2004 | Elder et al. |
| 2006/0057020 A1 | 3/2006 | Tufo |
| 2007/0119699 A1 | 5/2007 | Chambers et al. |
| 2007/0137489 A1 | 6/2007 | Luo |
| 2009/0064864 A1 | 3/2009 | Mann et al. |
| 2009/0098014 A1 | 4/2009 | Longstaff |
| 2014/0017135 A1 | 1/2014 | Boodaghians et al. |
| 2016/0038624 A1 | 2/2016 | Krosney |
| 2016/0310627 A1 | 10/2016 | Frazier |
| 2020/0376152 A1 | 12/2020 | Krosney |
| 2021/0093744 A1 | 4/2021 | Krosney |
| 2021/0361815 A1 | 11/2021 | Krosney |

FOREIGN PATENT DOCUMENTS

| | | | | |
|---|---|---|---|---|
| JP | H10314620 A | * | 12/1998 | |
| JP | 2914464 | * | 4/1999 | |
| JP | 200397816 A | * | 4/2003 | |
| JP | 4483602 B2 | * | 6/2010 | |

* cited by examiner

Figure 12A
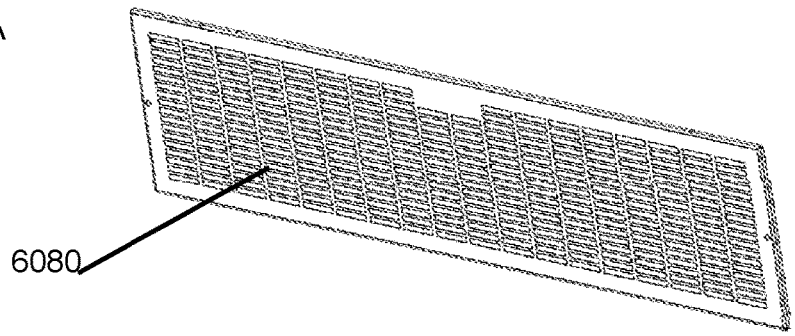
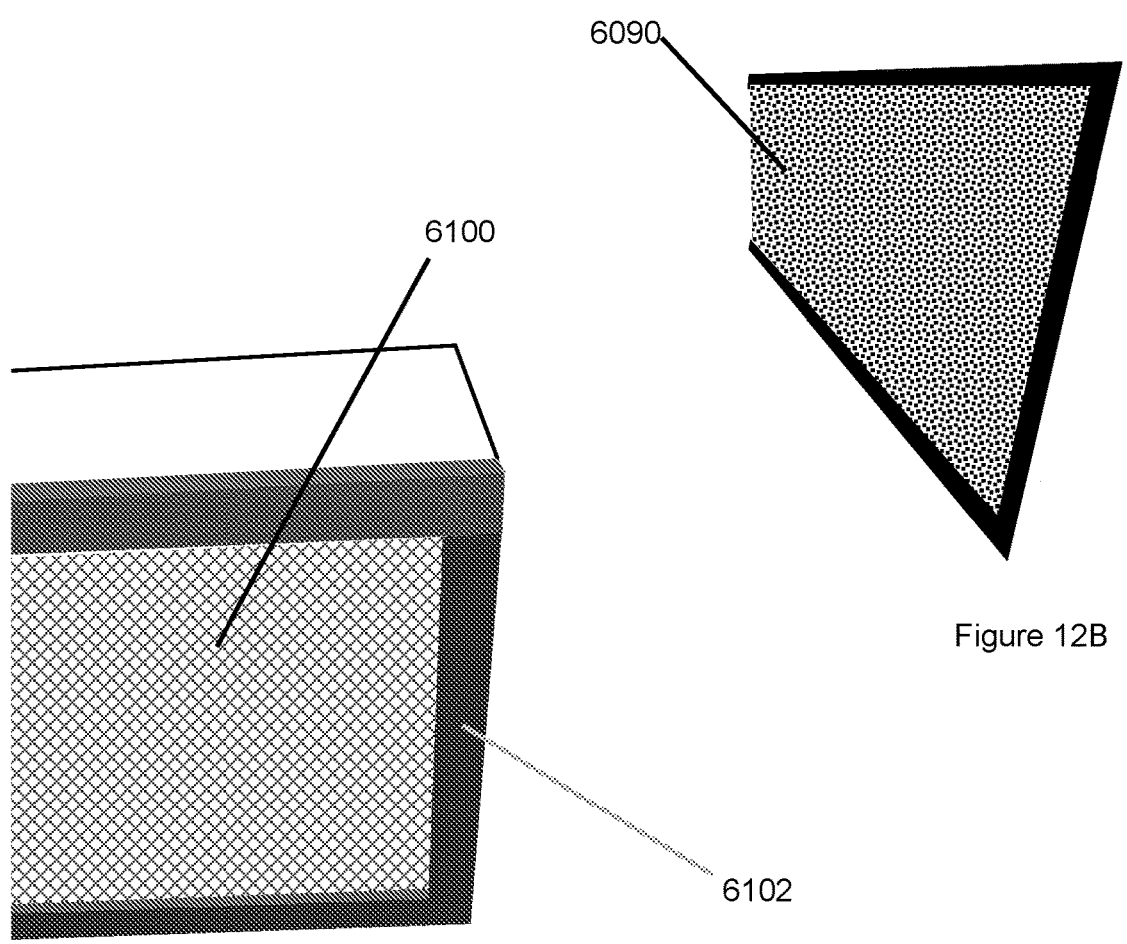
Figure 12B
Figure 12C

4850

AIR TREATMENT SYSTEM FOR VEHICLES

CROSS-REFERENCE TO RELATED APPLICATION

This patent application claims the benefit of Provisional U.S. Ser. No. 63/041,999, filed Jun. 21, 2020, which is incorporated herein by reference in its entirety.

FIELD OF THE INVENTION

Embodiments of the invention pertain to air treatment systems for use in heavy duty and public transportation vehicles.

BACKGROUND OF THE INVENTION

Various forms of air treatment systems exist. However, many of them have shortcomings for use in vehicles, and there is increasing need for better air treatment systems, especially in response to current concerns about transmission of viruses and other pathogens. There is a need to restore confidence to vehicle drivers and passengers in response to the public health issues such as the COVID pandemic.

SUMMARY OF THE INVENTION

An embodiment of the invention comprises an air treatment system for a vehicle, said vehicle having a forward-rearward direction and a sideways direction and an up-down direction, said directions being mutually orthogonal, said air treatment system being installed at or near a ceiling of said vehicle, said air treatment system comprising: an air intake that is oriented in a generally sideways direction; a forward air discharge that is located on a forward-facing side of said air treatment system, and is oriented in said forward direction and contains a generally forward-directed louver; a rearward air discharge that is located on a rearward-facing side of said air treatment system and is oriented in said rearward direction and contains a generally rearward-directed louver; and a downward air discharge that is located on a downward-facing side of said air treatment system and is oriented in said downward direction and contains a generally downward-directed louver, wherein said forward-directed louver comprises an upper vane that extends generally side-to-side and is generally forward-directed, and comprises a lower vane that extends generally side-to-side and is forward-directed, said upper forward-directed vane being closer to said ceiling than said lower forward-directed vane, said lower forward-directed vane pointing more downward than said upper forward-directed vane, wherein rearward-directed louver comprises an upper vane that extends generally side-to-side and is rearward-directed, and comprises a lower vane that extends generally side-to-side and is generally rearward-directed, said upper rearward-directed vane being closer to said ceiling than said lower rearward-directed vane, said lower rearward-directed vane pointing more downward than said upper rearward-directed vane, and wherein said downward-directed louver comprises a downward-directed-louver first-side vane that extends in a generally forward-rearward direction and is generally downward-directed, and comprises a downward-directed louver second-side vane that extends generally forward-rearward and is generally downward-directed, one of said vanes being vertical or closer to vertical, and the other of said vanes being less close to vertical, wherein said vanes that are vertical or closer to vertical are located, in said sideways direction, further away from said intake, and wherein said vanes that are less close to vertical are located closer to said intake.

An embodiment of the invention comprises an air treatment system for a vehicle, said air treatment system comprising: an air intake containing therein a filter; an air treatment region comprising therein a UV light source suitable to direct UV light from said UV light source at air passing through said air treatment region; a directed discharge blower and a bulk discharge blower, each of said blowers taking in air that has passed through said filter and said air treatment region, each of said blowers having a respective blower discharge; a directed discharge plenum, capable of receiving discharge from said directed discharge blower, said directed discharge plenum having, emanating therefrom, a plurality of directed discharge louvers at least some of which are not aligned with or are offset from said discharge of said first blower; and a bulk flow plenum, capable of receiving discharge from said bulk discharge blower, said bulk flow plenum having a bulk flow plenum exit louver, wherein said directed discharge blower and said bulk discharge blower are both driven by a first motor.

An embodiment of the invention comprises an air treatment system for a vehicle, said air treatment system comprising: an air intake in fluid communication with a vehicle interior space; a filter downstream of said air intake, said filter being housed in a filter housing that is generally impermeable through surfaces of said filter housing; an ultraviolet exposure region downstream of said filter, said ultraviolet exposure region comprising an Ultraviolet light source; a shield, said shield being suitable to block propagation of UV light rays from said Ultraviolet light source in certain directions; and an air moving device, suitable to move air from said air intake to a discharge, wherein a flowpath from said intake to said discharge comprises, in sequence, said intake, and said filter, and said ultraviolet exposure region, and a constriction, and said air moving device, and said discharge, wherein said shield has a shield longitudinal edge extending in a longitudinal direction and said filter housing has an external corner edge extending along said longitudinal direction, wherein said constriction in said flowpath of air from said inlet to said discharge is formed at least in part by said shield longitudinal edge and said filter housing external corner edge.

Embodiments of the invention can include various designs of shielding to contain ultraviolet light within the system.

Types of vehicles in which embodiments of the invention can be used include a van, a recreational vehicle, a small bus, a school bus, a transit bus, a shuttle bus, a paratransit vehicle, an ambulance, an emergency vehicle, or a vehicle with a rated capacity of 7 to 50 people.

BRIEF DESCRIPTION OF THE ILLUSTRATIONS

Embodiments of the invention are further described, but are in no way limited, by the following illustrations.

FIG. 1, for a first embodiment of the invention, is a top view of a bus showing possible placement of two air treatment units.

FIGS. 12A, 12B and 12C shows photographs of the grille, pre-filter and HEPA filter respectively.

Figure 22A:
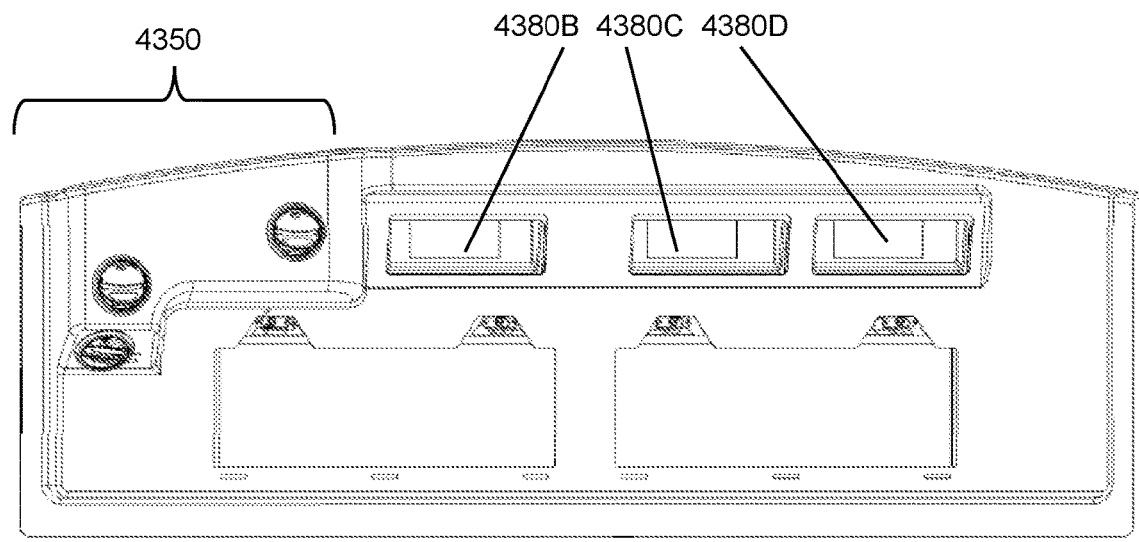
Figure 22B:
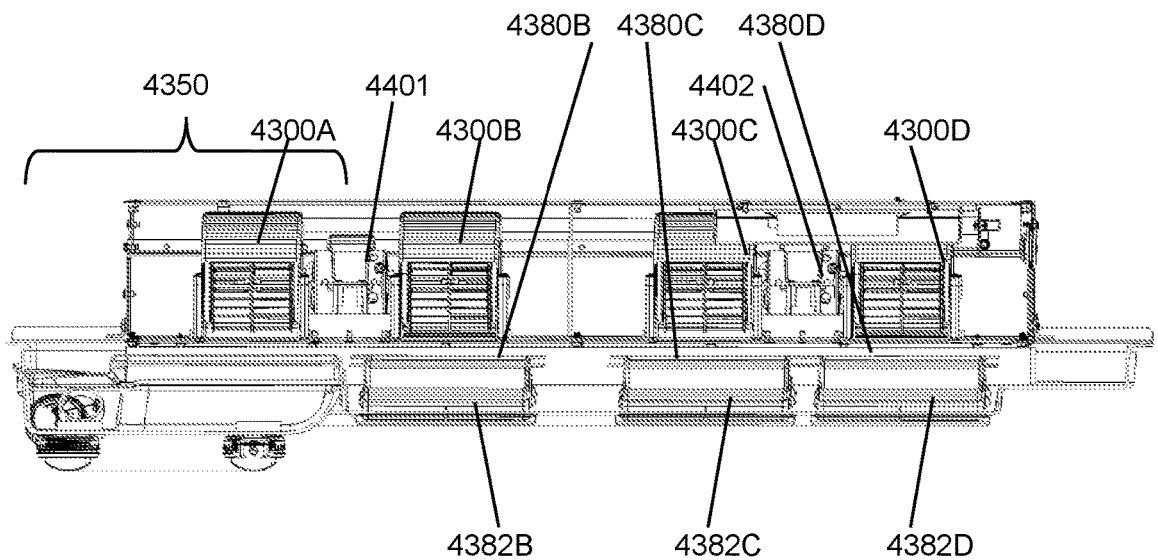
Figure 22C:
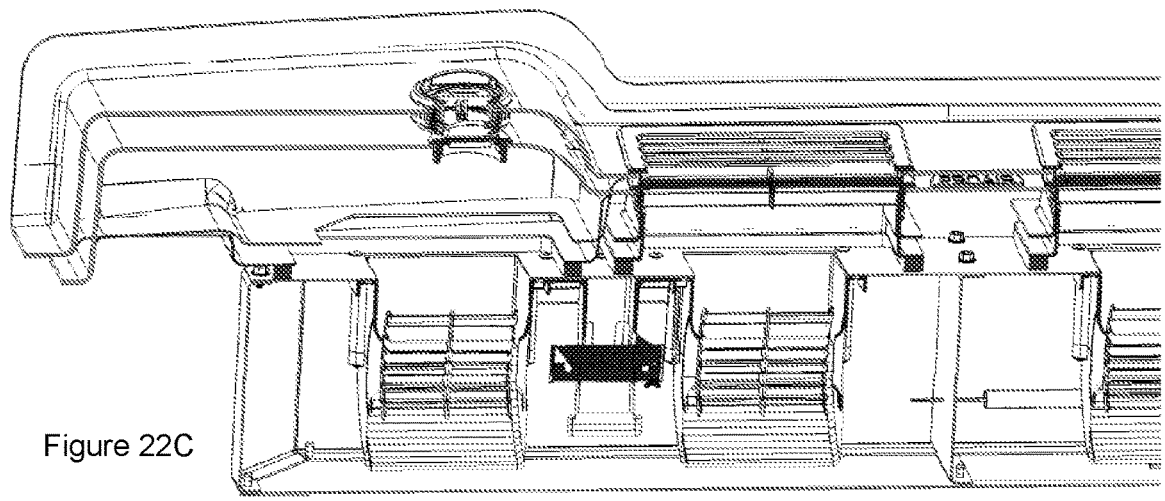
Figure 22D:
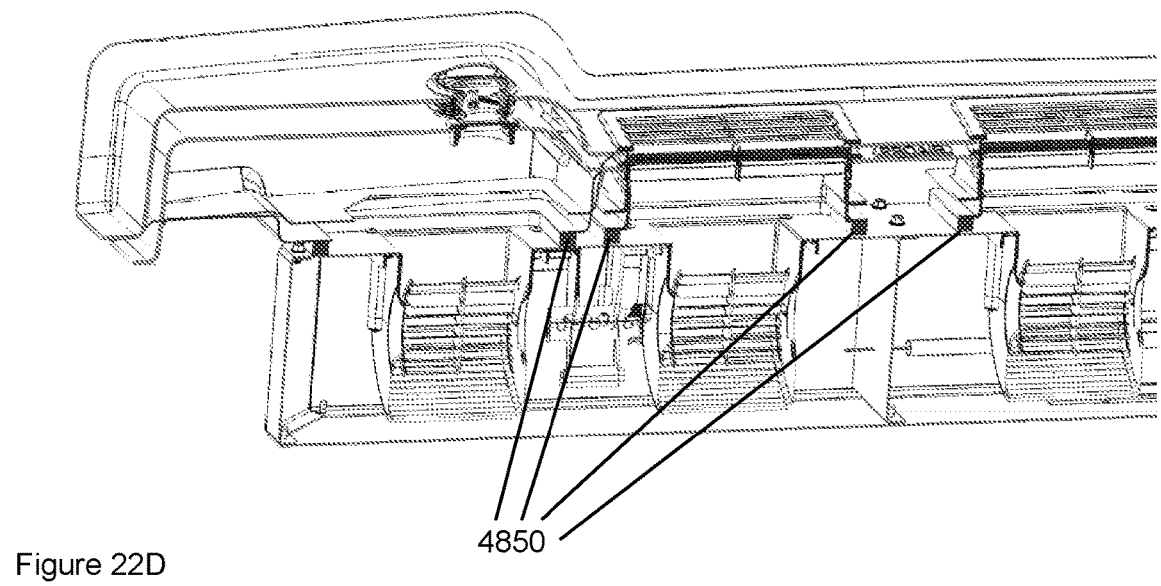

FIG. 22A shows a frontal view of the air treatment unit with its front removed. FIG. 22B shows a top view. FIGS. 22C and 22D show bottom views.

Figure 23A:
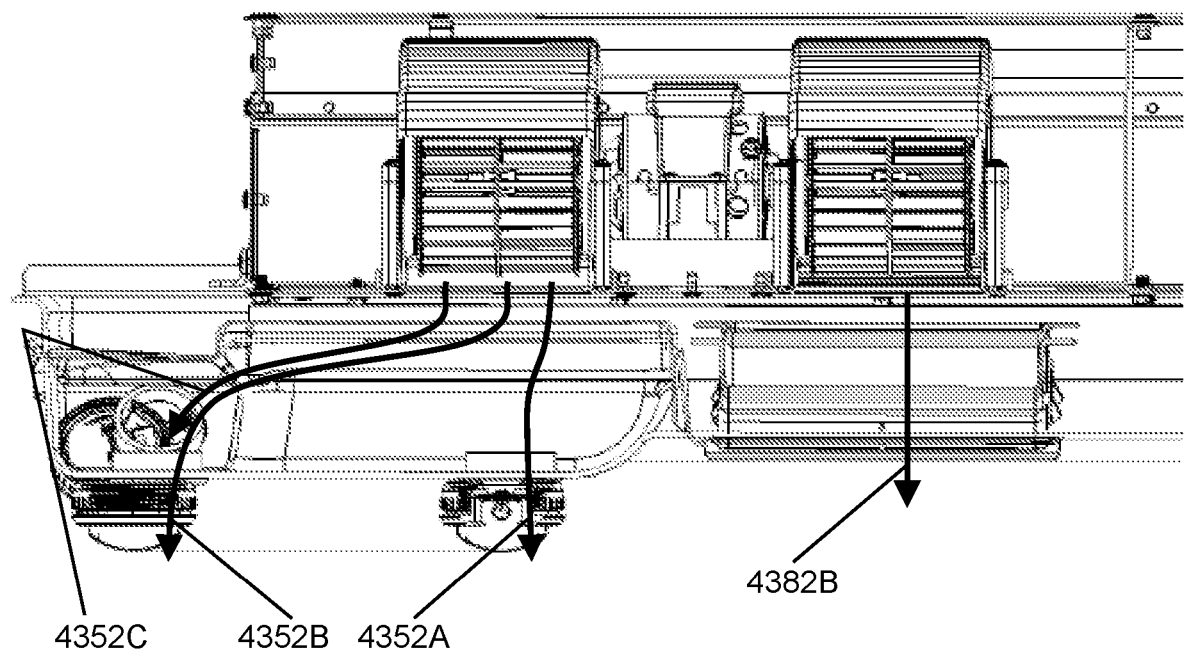
Figure 23B:
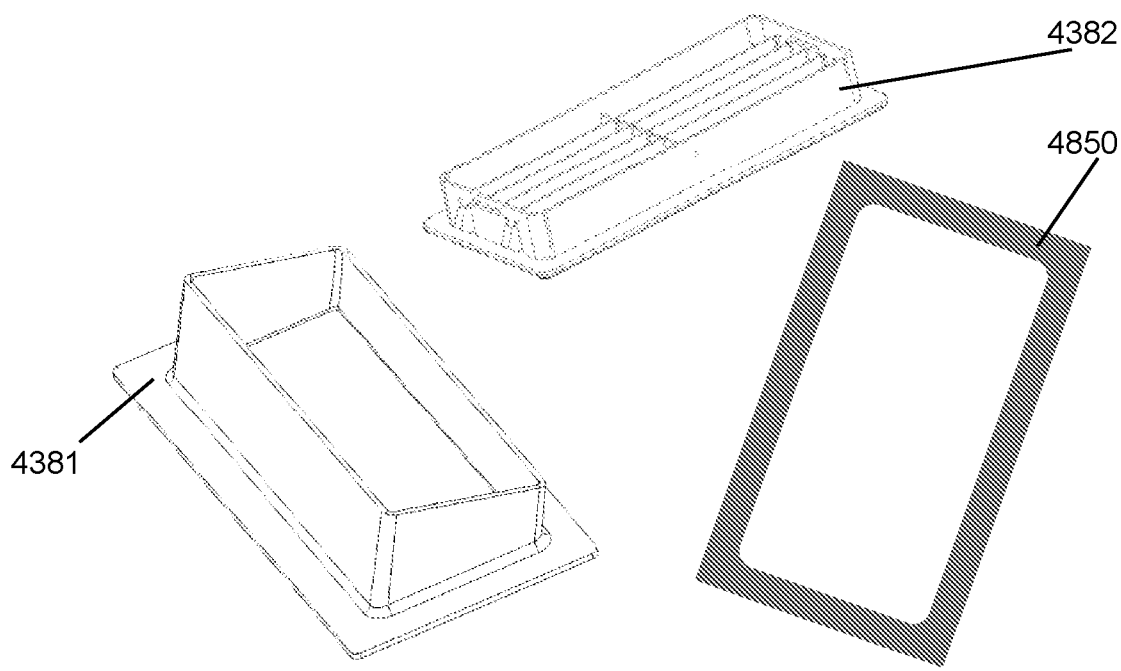
Figure 23C:
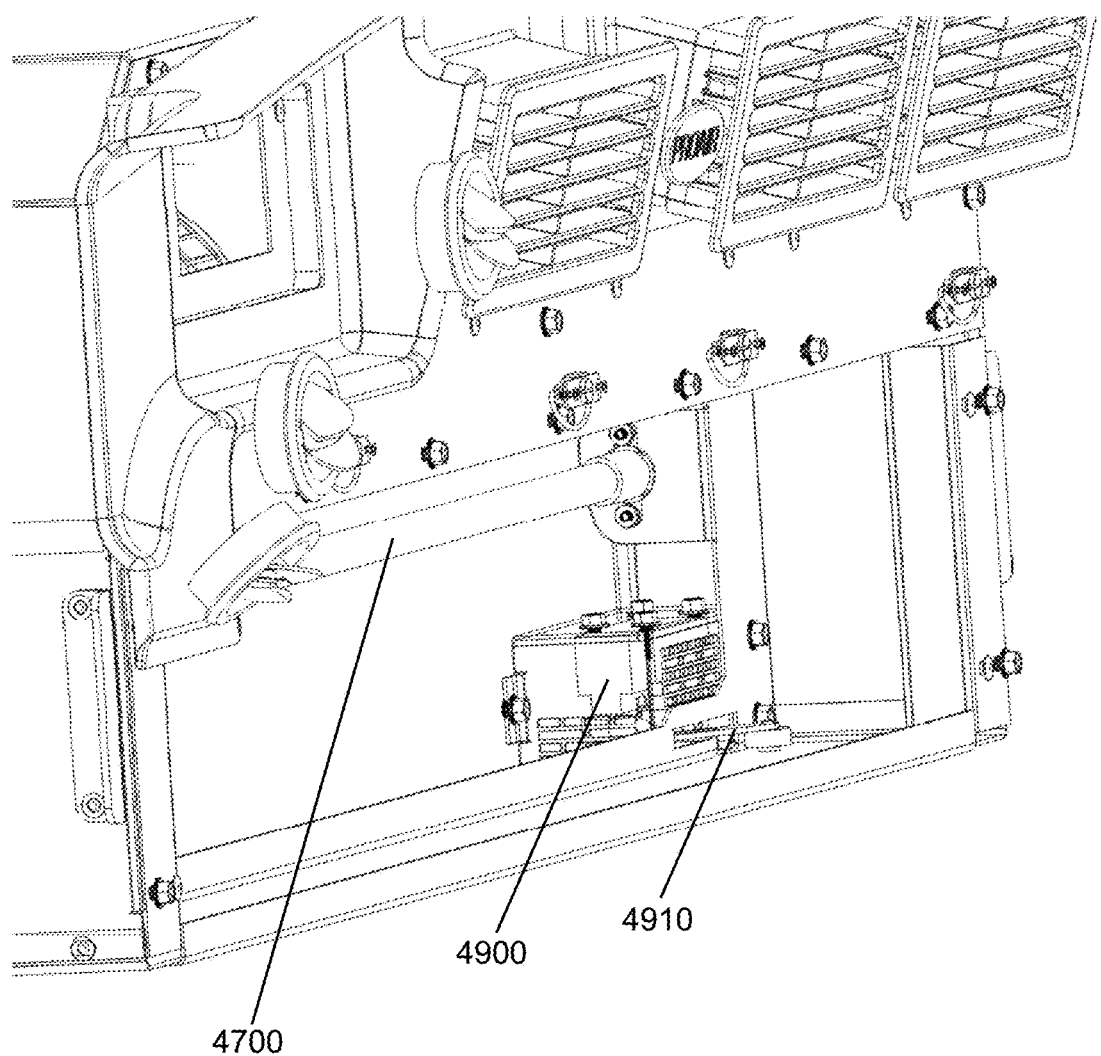

FIG. 23A shows possible air flow patterns. FIG. 23B shows a louver, a bezel and a foam gasket. FIG. 23C shows a switch for a safety interlock.

Figure 24:
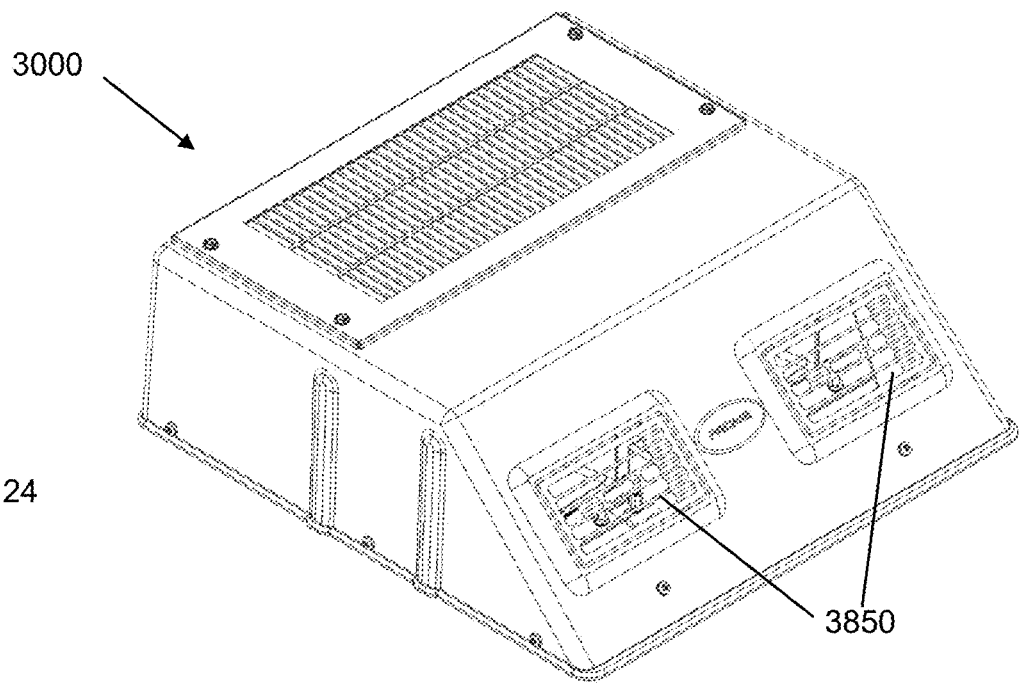

FIG. 24 illustrates, for yet another embodiment, an external view of an air treatment unit.

Figure 25:
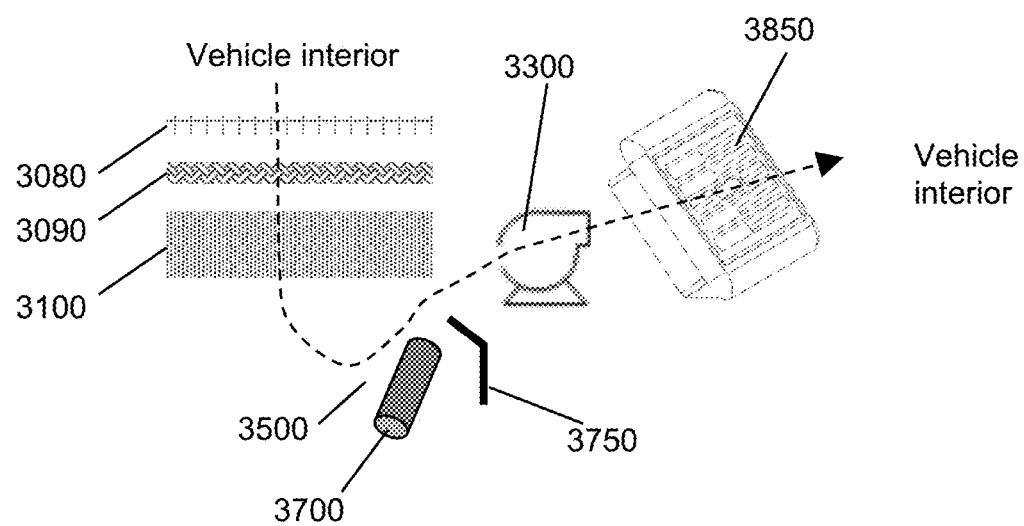

FIG. 25 is a schematic illustration showing the flowpath of air through or past various internal components of the air treatment unit.

Figure 26:
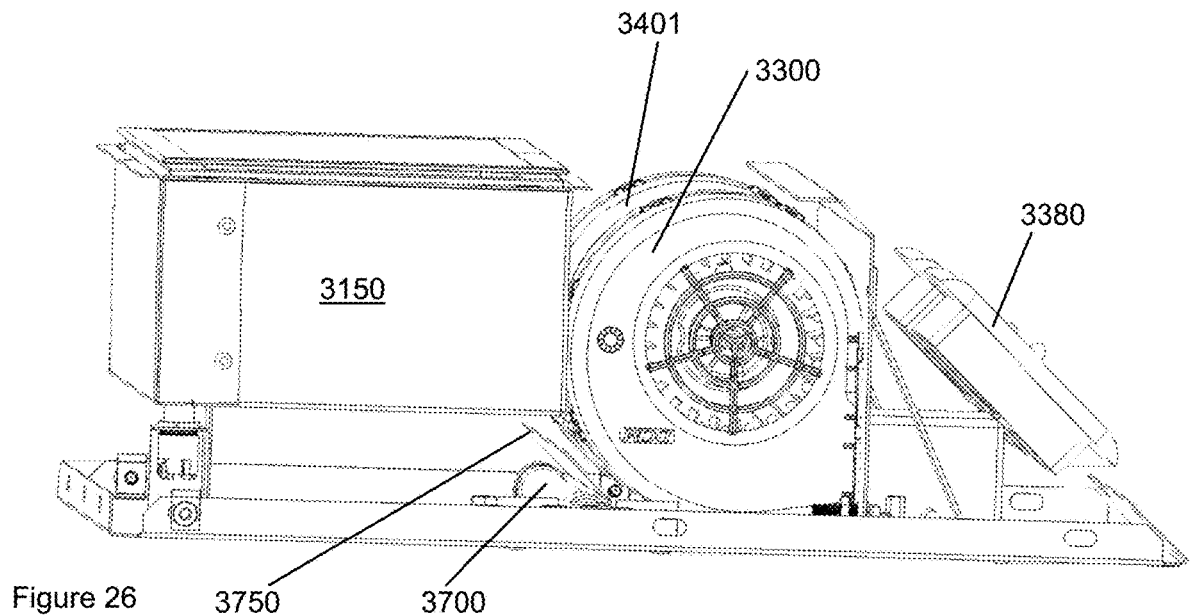

FIG. 26 is a slightly angled side view of the air treatment unit with certain components omitted for clarity of illustration.

Figure 27:
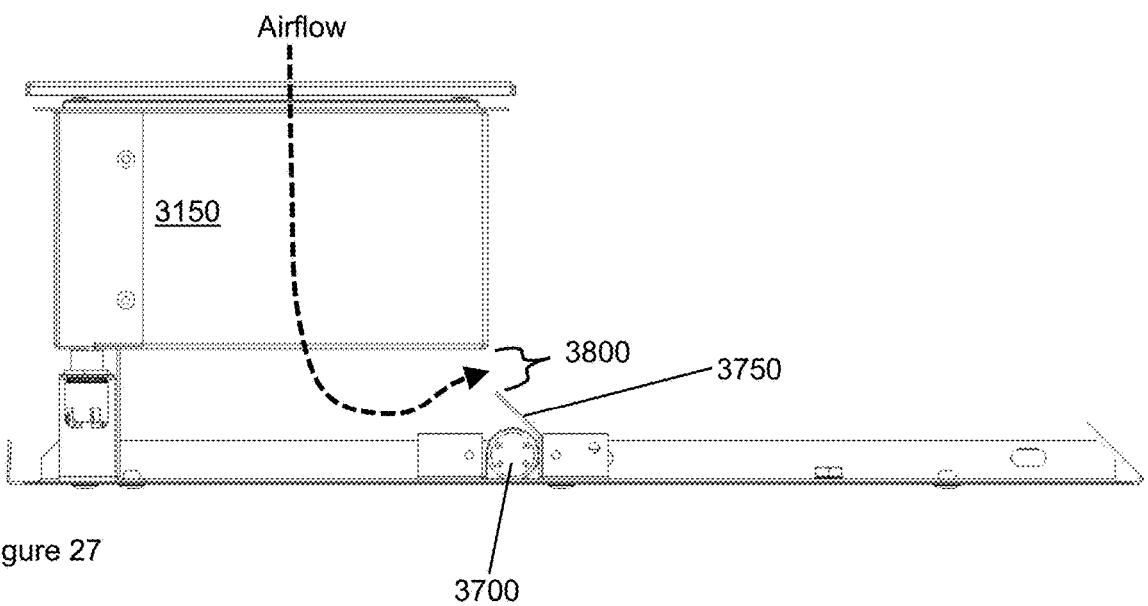

FIG. 27 is a similar view that is a true side view.

Figure 28:
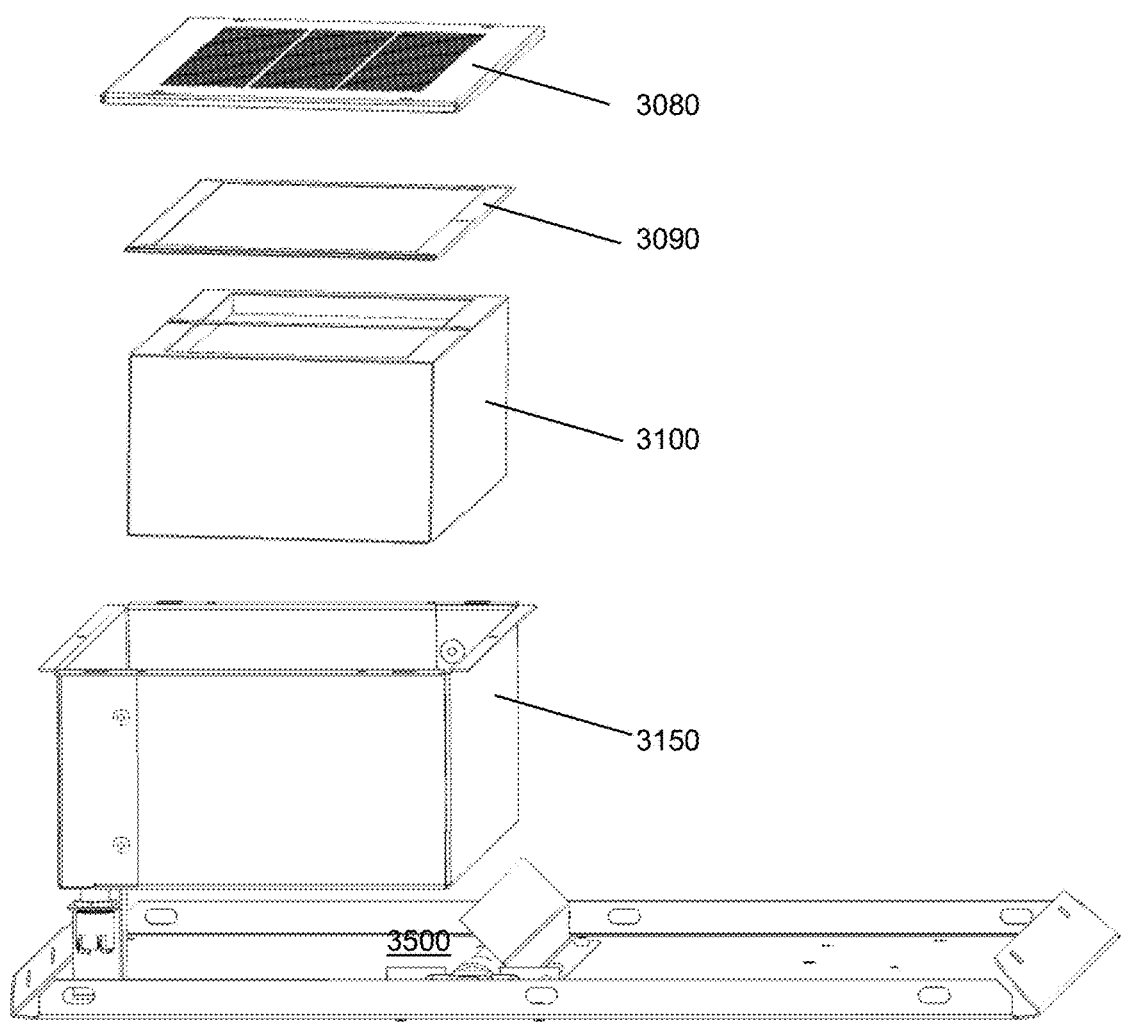

FIG. 28 is a similar view, in perspective, and additionally showing the filter, pre-filter and grille shown exploded.

Figure 29A:
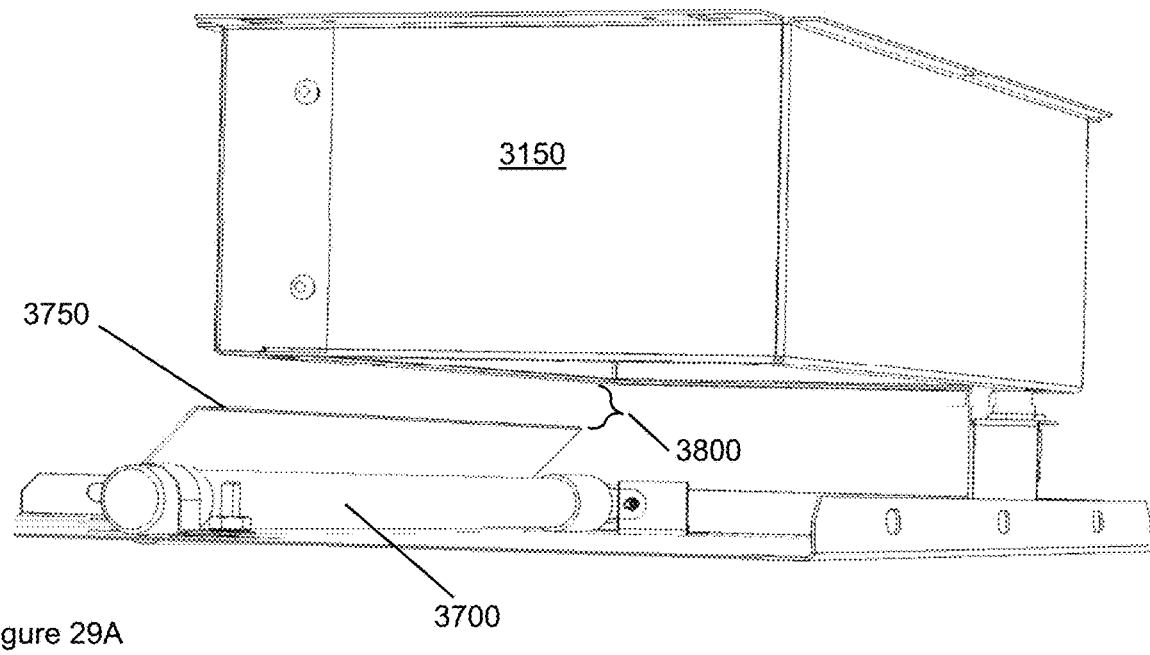

FIG. 29A shows, in perspective, the two longitudinal boundaries of the constriction.

Figure 29B:
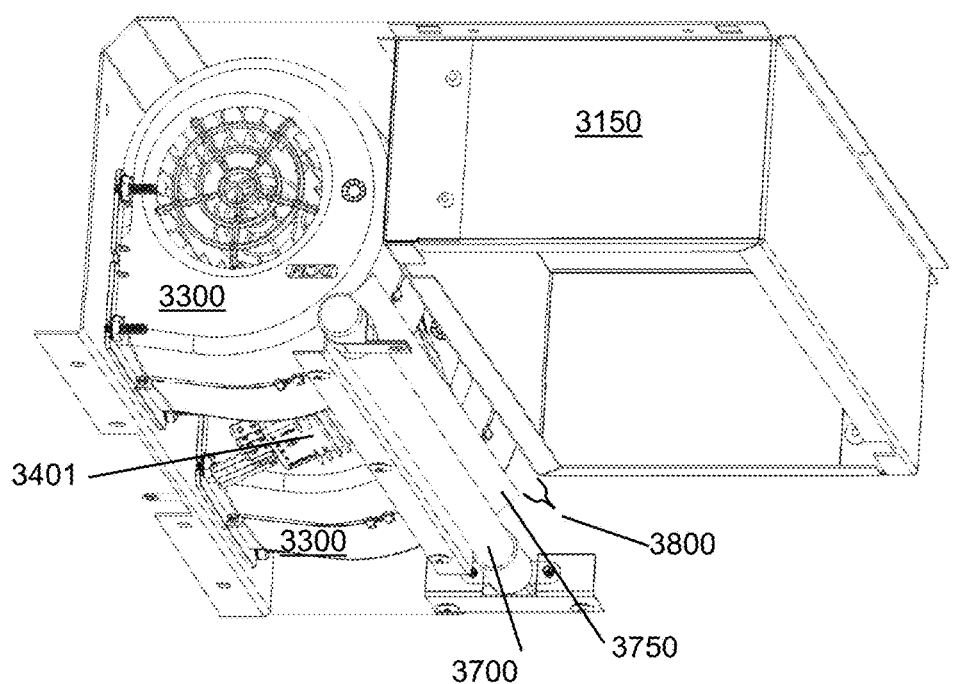

FIG. 29B also shows the two longitudinal boundaries of the constriction, but from a perspective that is more from below, and with different components omitted for clarity of illustration.

DETAILED DESCRIPTION OF THE INVENTION

A significant current public health concern is transmission of viruses such as COVID-19. The COVID-19 virus is known to have a survival time, outside of a host, of hours or days depending on environmental conditions, and transmission of this virus is known to occur both by contact with surfaces and by inhalation of air. In view of the importance of transportation including public transportation, this creates a particular need for air treatment in vehicles. For example, school buses and paratransit and other small group transport have need of such systems, as do larger vehicles also. In general, such vehicles may include vans, recreational vehicles, small buses, school buses, transit busses, shuttle buses, paratransit vehicles, ambulances, emergency vehicles and other types of vehicles.

In such a situation, there is a need for air flow distribution patterns that effectively mix and process the interior air of the vehicle as thoroughly as possible, with circulation patterns that reach as much of the vehicle interior as possible. This is for the benefit of both passengers and the driver. Design features of the air treatment units can advance this goal. Internal components of the air treatment unit need to be effective for capturing or killing pathogens such as viruses. It is recognized that it is desirable to provide a certain number of air changes per hour of the bulk volume of interior air of the vehicle. However, there also is specific interest in providing a biologically safe localized environment for the driver by providing an adequate flow of disinfected air directed at the immediate vicinity of the driver.

Air filtration units for vehicular (mobile) applications are subject to requirements that might not have been met by units that are used in stationary applications. One such requirement is the need for fire resistance, as governed by Federal Motor Vehicle Safety Standard (FMVSS) No. 302 for the safety of vehicle occupants from vehicle fires. Fire safety can be achieved, for example, by appropriate choice of materials of construction or by application of fire-resistant coatings. Another factor that is specific to mobile applications is that the devices are subject to vibration caused by interaction with the road, which could arise not only from the vehicle traveling on a typical paved road, but also from the vehicle traveling on rough terrain such as a gravel road or an unpaved road. This can mean, for example, that certain seals and related features may need to be mechanically robust.

Reference is now made to the FIGS. 1-17, showing an embodiment that may be referred to as HEPA-6.

In general, in an embodiment of the invention, the vehicle may have a defined or enclosed vehicle interior space containing air that may need to be treated. An air treatment system 6000 of an embodiment of the invention may comprise an air intake 6060 in communication with the vehicle interior space; an air discharge in communication with the vehicle interior space; and an air-mover to cause air to move from the air intake 6060 through an air treatment region and to the air discharge.

Figure 2:
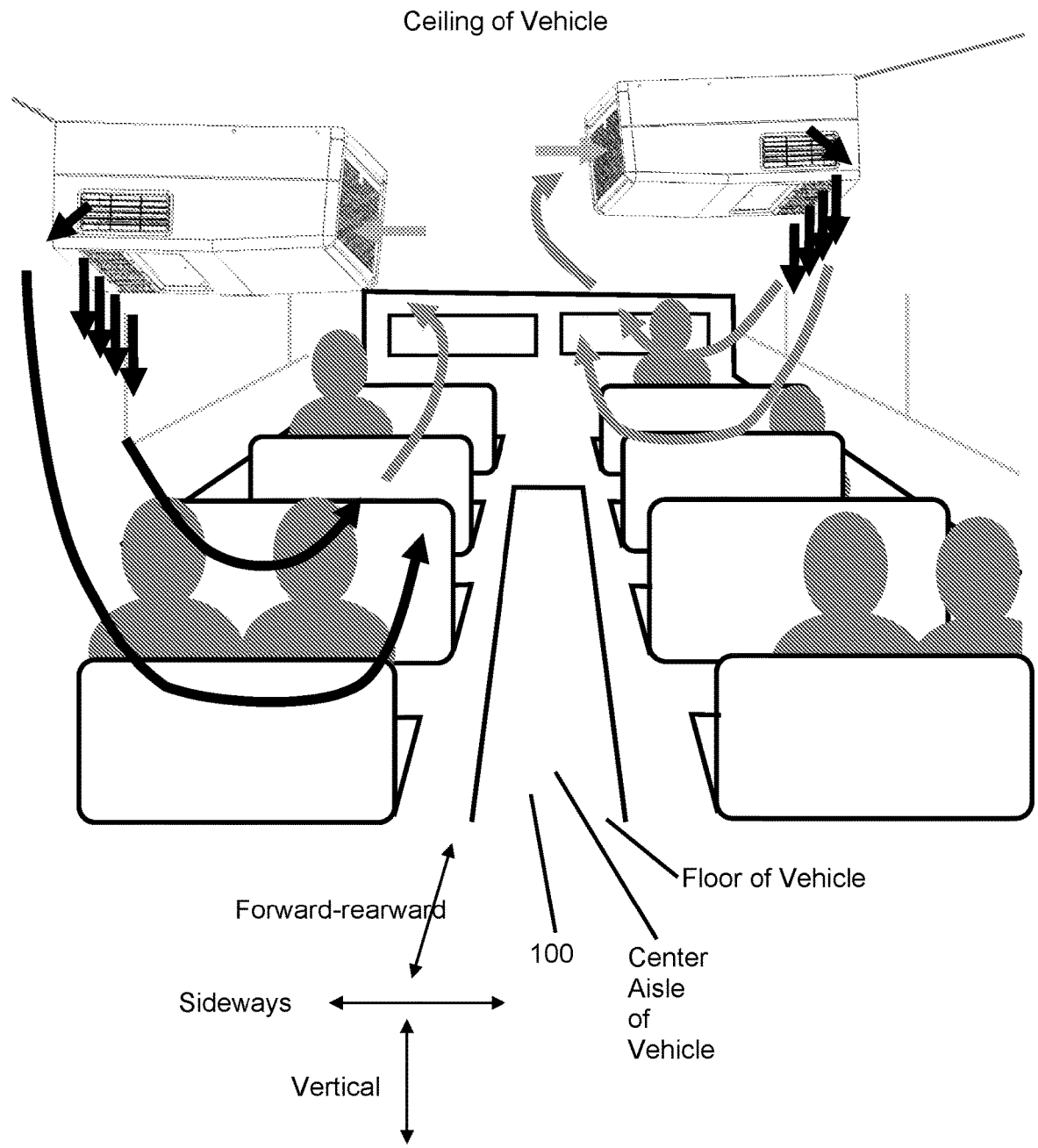
FIG. 2 shows a three-dimensional interior view of the bus showing the two air treatment units and associated air flow patterns.

An embodiment of the invention may be an air treatment unit 6000 suitable to be installed in the passenger region of a vehicle, such as at or near the ceiling of the vehicle. In an embodiment of the invention, the air treatment unit 6000 may have an overall shape that is elongated in one direction and may have a much smaller dimension in another direction. The relatively elongated direction of the air treatment unit 6000 may correspond to the forward-rearward direction of a vehicle. The relatively smaller dimension of the air treatment unit 6000 may correspond to the vertical direction of the vehicle. Coordinate directions are indicated in FIG. 2. The air treatment unit 6000 may be suitable to be mounted at or near the ceiling of the vehicle interior.

Figure 1:
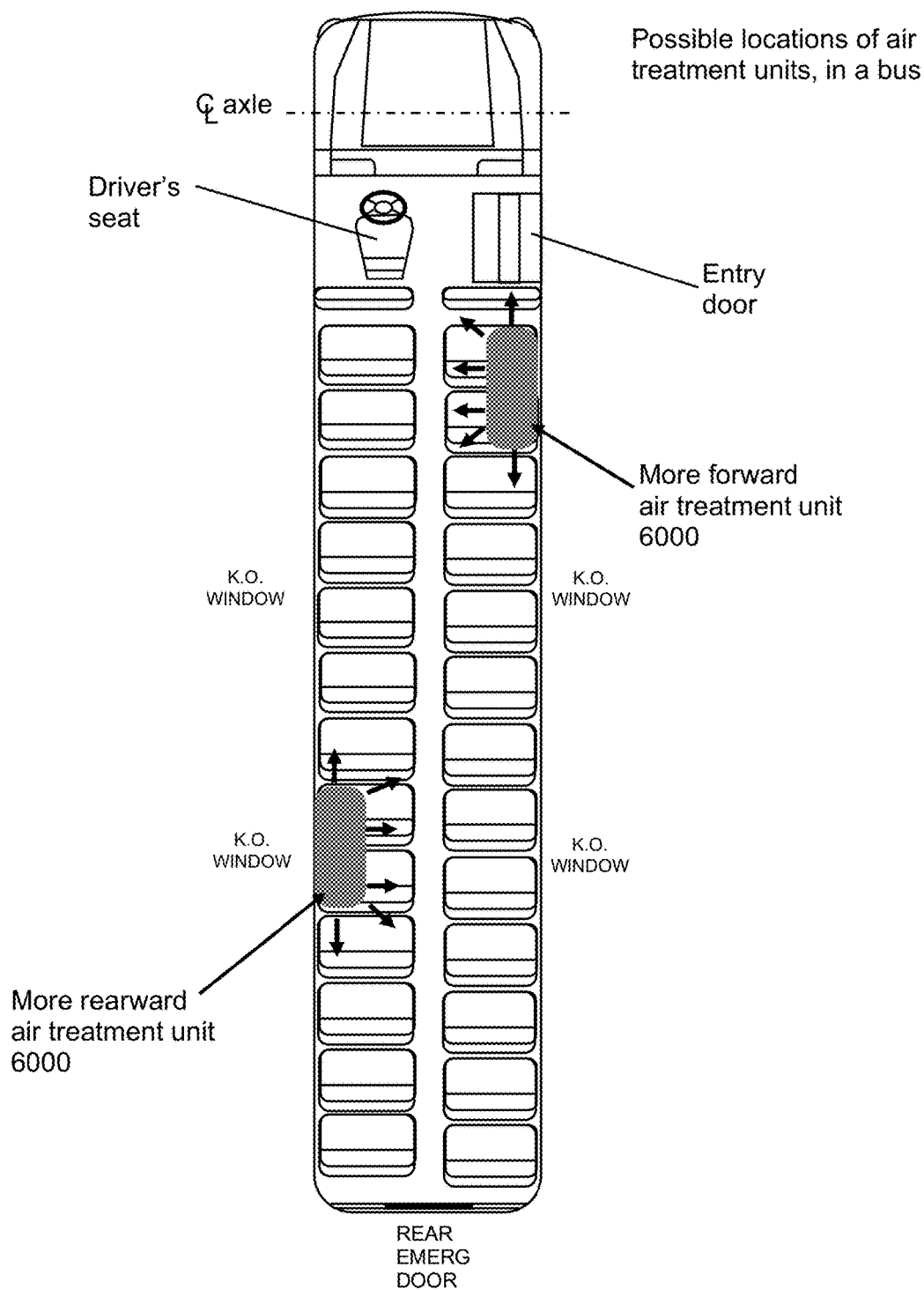

FIGS. 1 and 2 show one possible way of mounting two such air treatment units 6000 in a bus. The vehicle may have a central aisle, and the air treatment unit 6000 may be suitable to be mounted so that it avoids occupying space in the central aisle. One air treatment unit 6000 may be mounted on each side of the central aisle. It is not necessary that the two air treatment units 6000 be located at the same forward-rearward position within the vehicle, and it perhaps is preferable that they be located at different forward-rearward positions within the vehicle. For example, one such unit 6000 could be placed closer to the driver, on the opposite side of the vehicle from the driver. The other unit 6000 could be placed further toward the rear of the vehicle, on the side opposite the first unit 6000. In general, proportions and installation locations other than those shown here are also possible.

FIG. 2 shows an external view of two air treatment units 6000 of an embodiment of the invention, in position as they might be installed in a vehicle, viewed somewhat from below, from the rear of the vehicle. In an embodiment, within the vehicle interior, the air treatment unit 6000 may be mounted generally above the heads of the seated passengers, but may be located so as to leave a full-height unobstructed ceiling in a central aisle of the vehicle.

Possible air flow patterns of embodiments of the invention are also illustrated in FIG. 2, although not in as detailed a manner as in later Figures. In an embodiment, with respect to the orientation in which the air treatment unit 6000 is typically mounted in a vehicle, air may enter the air treatment unit 6000 in a generally horizontal direction, which may be from the central aisle of the vehicle, which may be a lateral (sideways) direction with respect to the overall vehicle directions. In an embodiment, air may be discharged from the air treatment unit 6000 in a forward direction and in a rearward direction and in a downward direction. In an embodiment, a certain design of fixed louver may be provided to spread out the airflow as described elsewhere herein.

Figure 5:
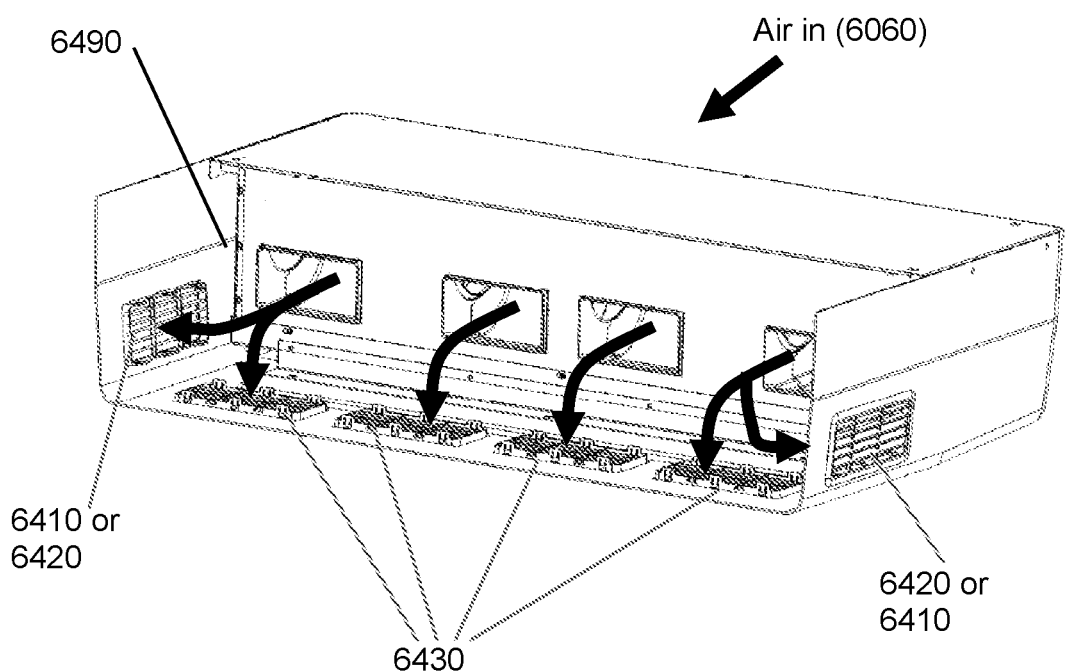
FIG. 5 is a view similar to FIG. 4B, showing air flow patterns in the plenum.
Figure 6A:
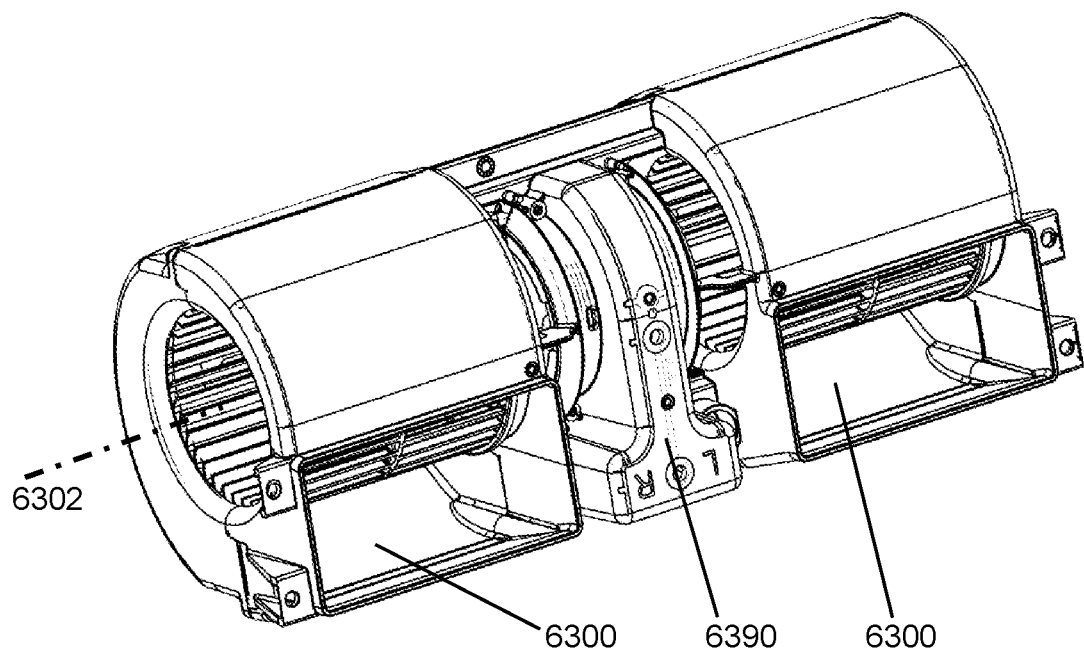
FIG. 6A shows a motor with a centrifugal blower attached at each end of the motor and driven by the motor shaft.
Figure 6B:
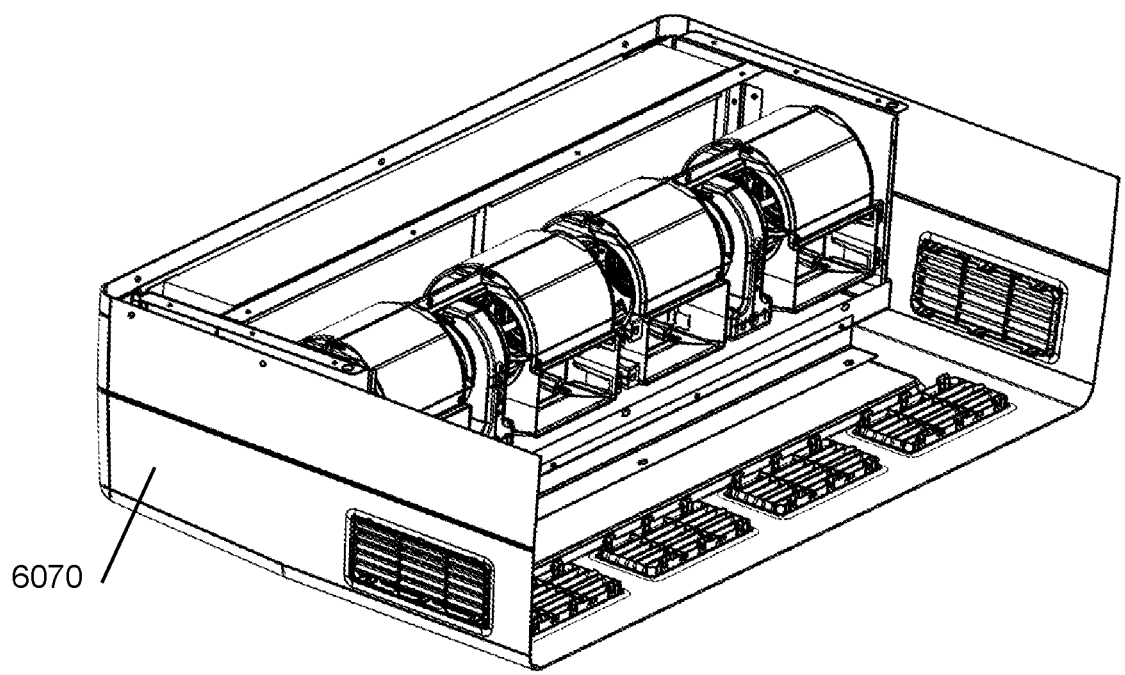
FIG. 6B shows two such motors and four such blowers mounted inside an air treatment unit.
Figure 7:
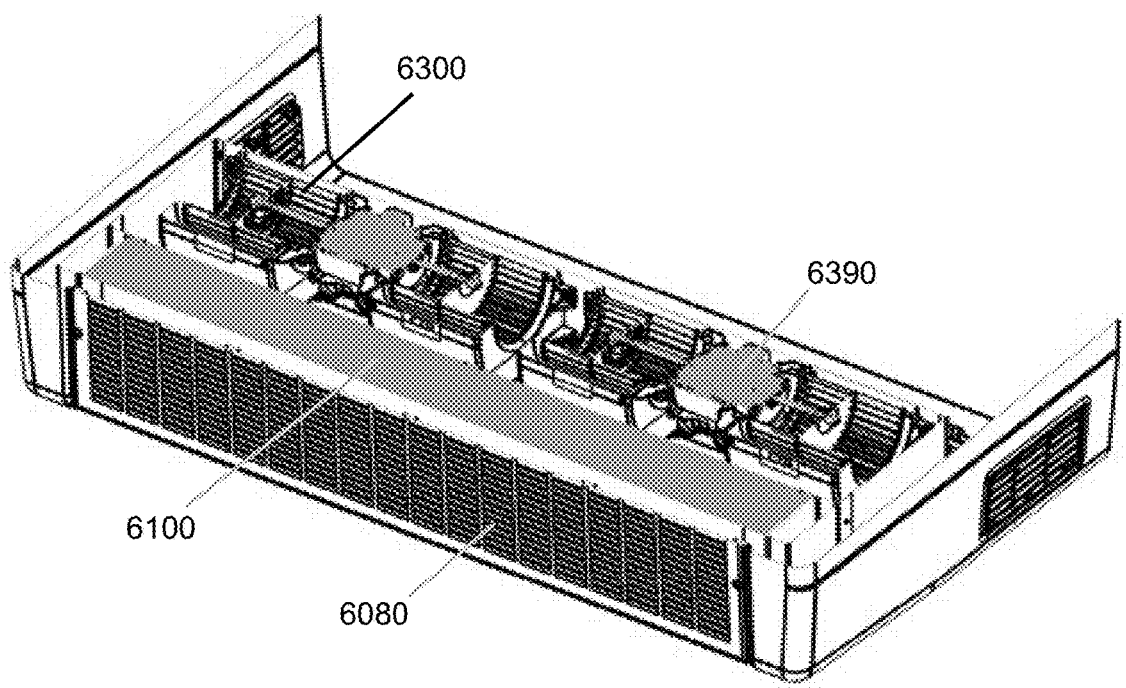
FIG. 7 is a sectional view showing the grille, HEPA filter, motors and blowers.
Figure 8:
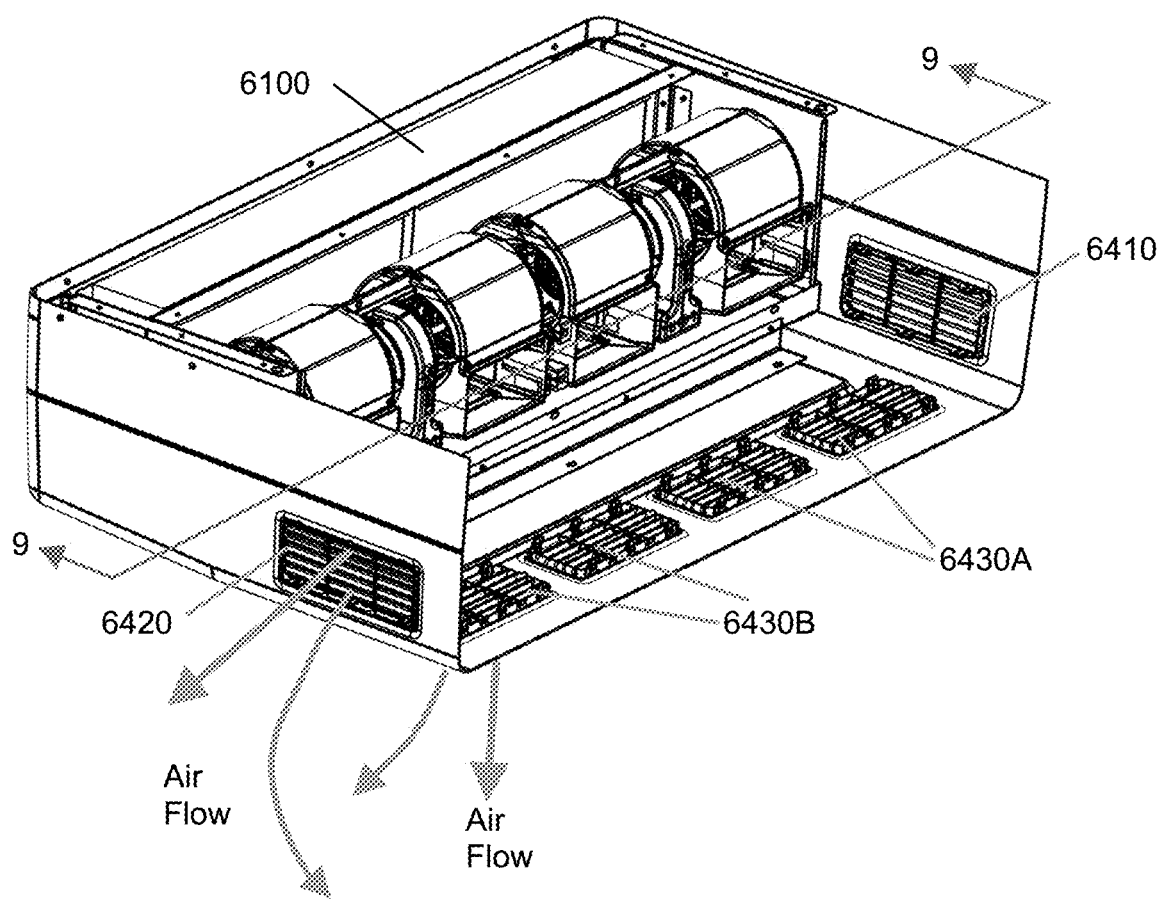
FIG. 8 shows the interior of the shroud and plenum, the blowers and the various louvers.
Figure 9:
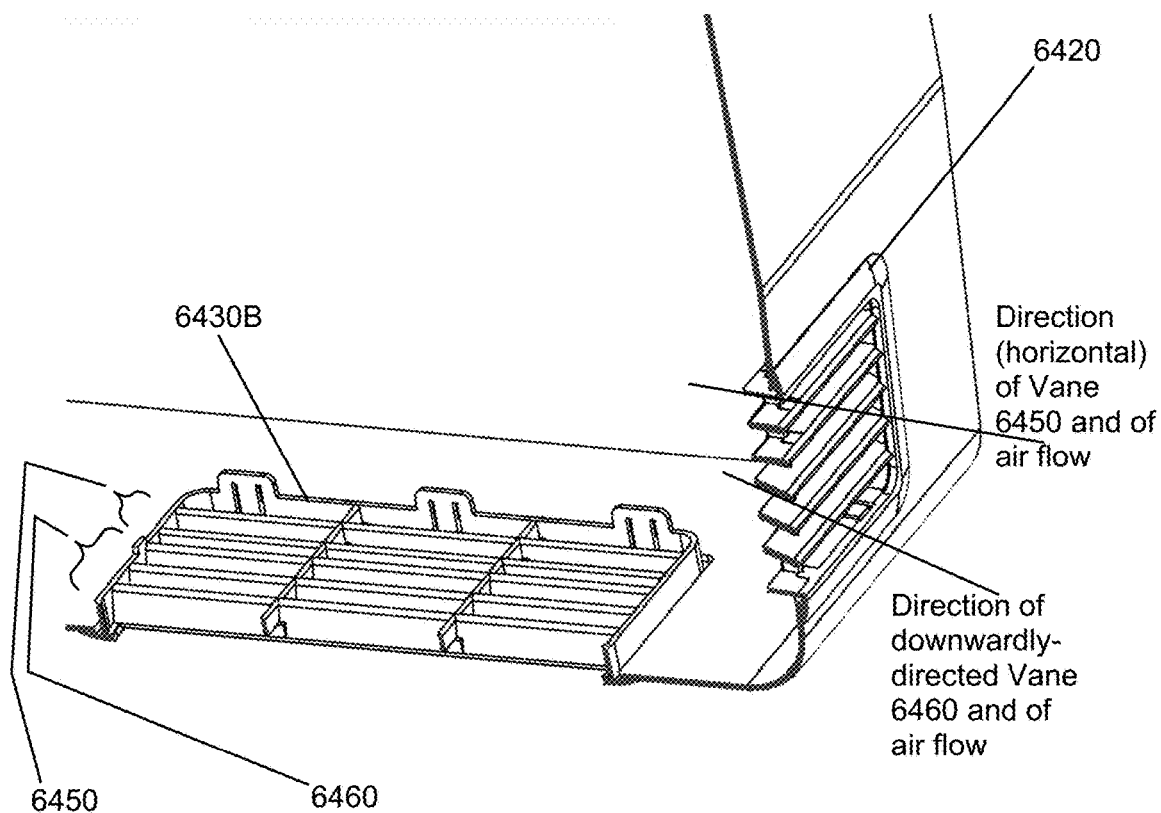
FIG. 9 shows a close-up view of the shroud and plenum and certain louvers and their vanes.
Figure 10A:
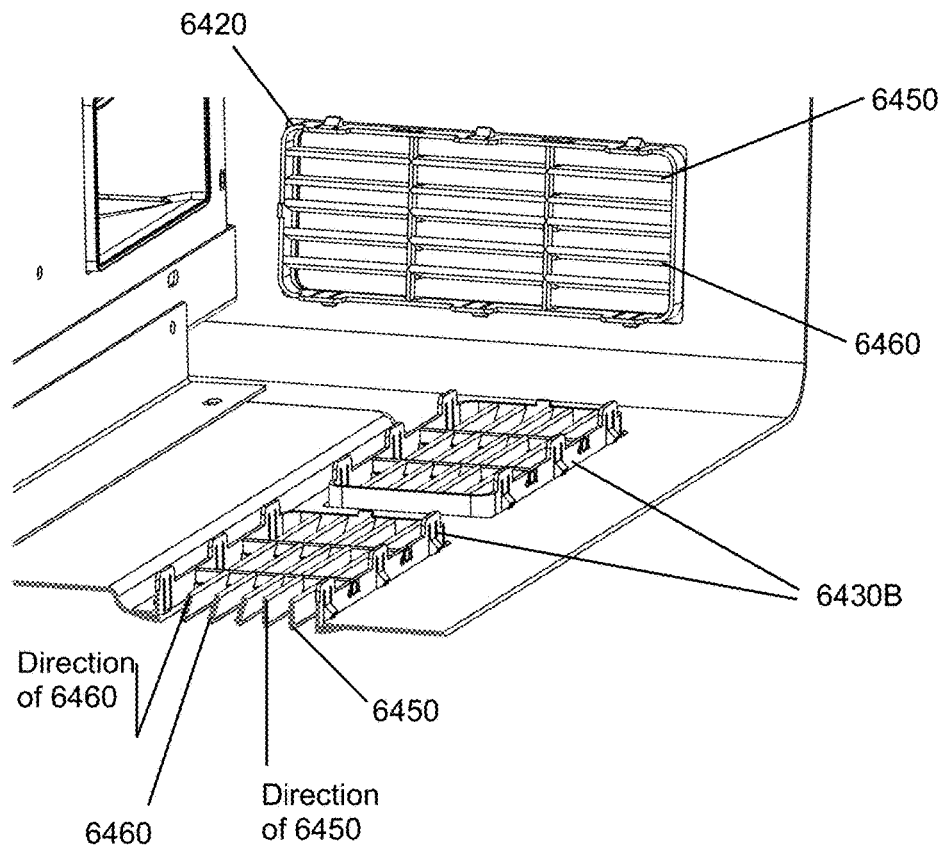
FIGS. 10A and 10B are additional views similar to FIG. 9.
Figure 10B:
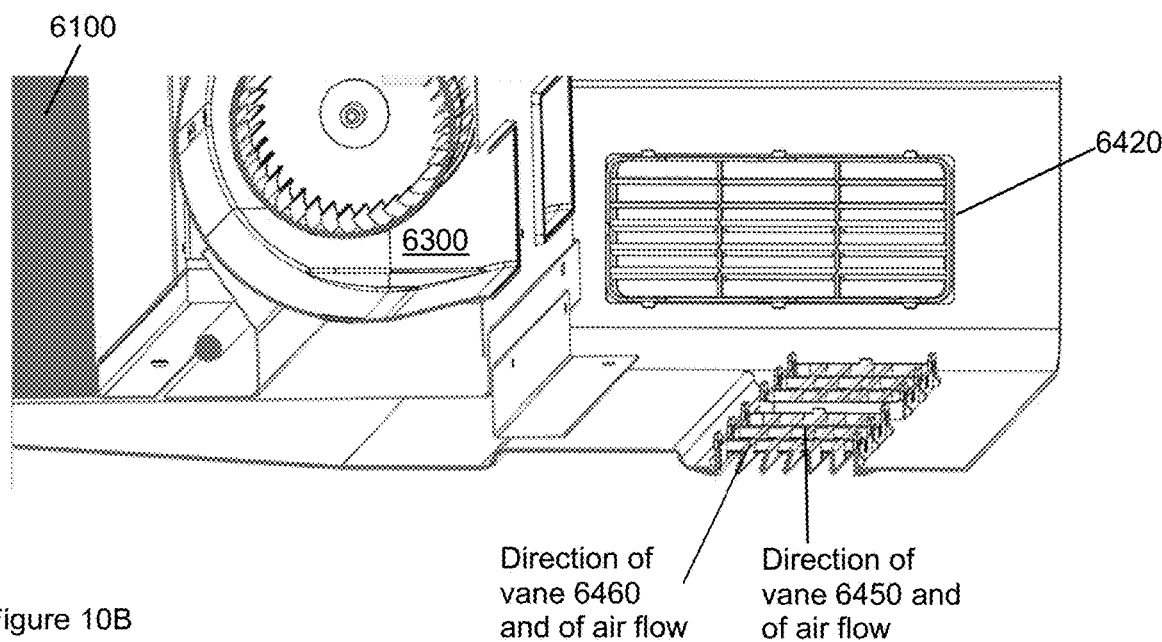
Figures 11A, 11B:
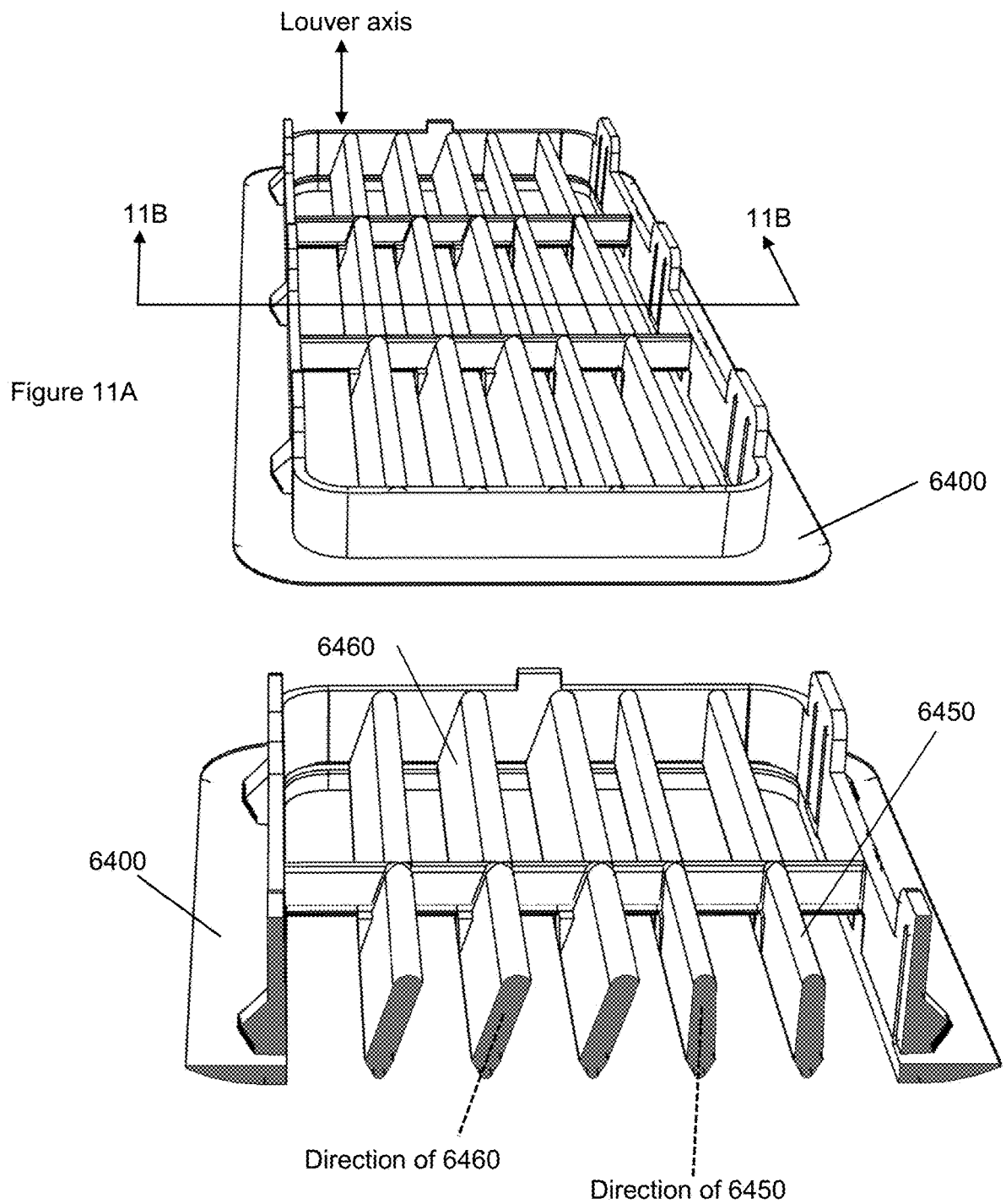
FIGS. 11A and 11B are additional views specifically of the louvers and their vanes.

Referring now to FIG. 5, in an embodiment, air may be discharged through a vent directed in an approximately forward direction with respect to the overall vehicle layout, through a generally forward-directed louver 6410. Air may be discharged through a vent directed in an approximately rearward direction with respect to the overall vehicle layout, through a generally rearward-directed louver 6420. Air may be discharged in an approximately vertically downward direction through four discharge vents 6430 each approximately corresponding to one of the blowers. Other configurations are also possible. Further details about the air flow patterns are discussed elsewhere herein.

Overview of Flow-Related Internal Components

Within the air treatment system 6000, the air-mover may typically comprise one or more centrifugal blowers, as are known in the industry. Alternatively, the air mover could be one or more fans, or other device adapted to cause air to move.

Figure 3:
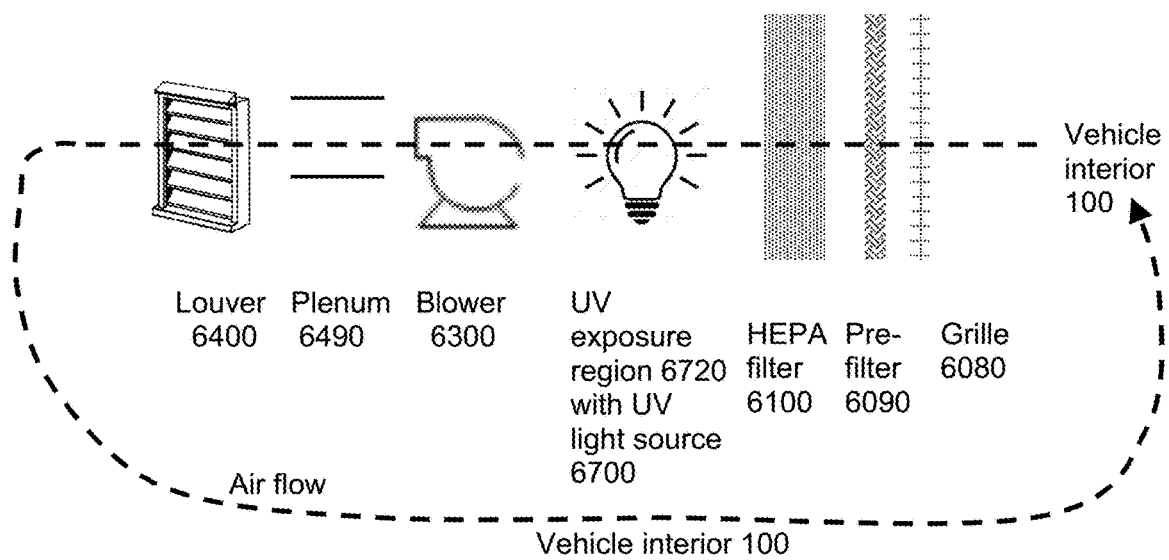
FIG. 3 is a schematic illustration showing the flowpath of air through or past various internal components of the air treatment unit.
Figure 4A:
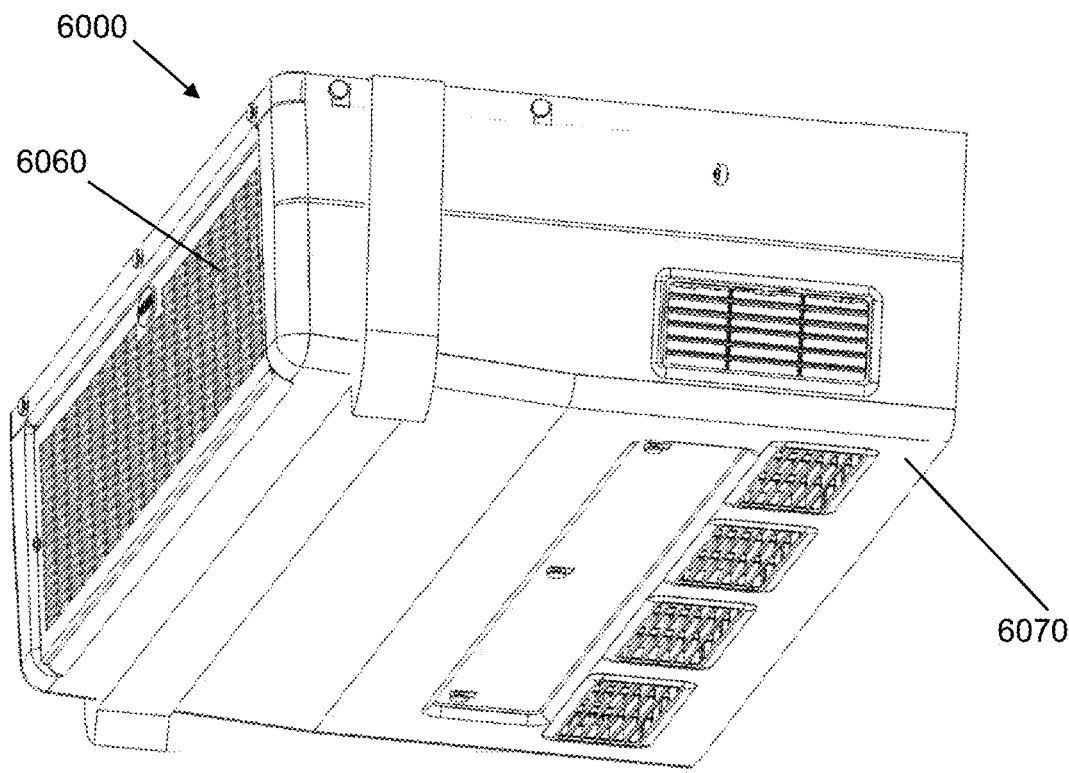
FIG. 4A is a three-dimensional view, from below, of the exterior of an air treatment unit of an embodiment of the invention.
Figure 4B:
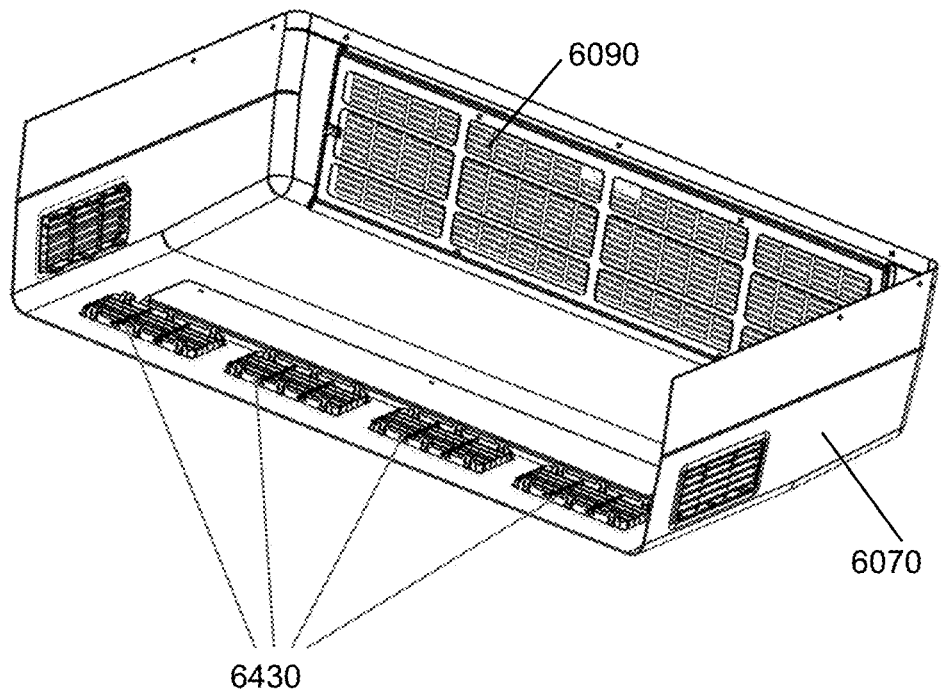
FIG. 4B is a three-dimensional view of the interior of the shroud of the air treatment unit, from above.

As illustrated in FIG. 3, the sequence of air flow may be that air is taken in from the vehicle occupant space 100 and enters the air treatment system 6000 by flowing through a grille 6080, then through a pre-filter 6090, and then through the HEPA (High efficiency Particulate Air) filter 6100. After leaving the HEPA filter 6100, the air may enter the air treatment region or UV exposure region 6720, where it may be exposed to Ultraviolet (UV) light. From there, the air may pass to the blower intake 600, through the blower 6300, out of the blower 6300 and through the air discharge plenum 6490 and air discharge vents, from which the air returns to the vehicle interior space 100. It can be noted that such arrangement effectively protects the UV lights from dust and particulates, because such dust and particulates would have already been filtered out by the pre-filter 6090 and HEPA filter 6100 during the normal sequence of air flow. It can also be noted that locating the UV light source as illustrated has the effect of using certain components such as the HEPA filter 6100 and the blowers 6300 themselves to somewhat block escape of UV light out of the air treatment region 6720 into the occupant interior space of the vehicle. It can also be noted that with respect to the downstream direction of airflow, escape of UV light from the air treatment region 6720 is blocked at least by the blower(s) 6300 and louvers, and possibly by other features not illustrated in FIG. 3. It can be understood that other geometric arrangements are also possible. The presence of a UV light source is optional.

The flowrate of air through the air treatment unit 6000, and the number of air treatment units 6000, may be chosen in combination with the size of the vehicle interior space to provide a desired number of air changeovers per hour and desired flow characteristics through the air treatment region.

Louvers and Air Flow Details

Referring now to FIGS. 4A-11B, in an embodiment of the invention, as described, air may be discharged in several different directions to promote desired airflow patterns within the vehicle. There may be a forwardly-discharging vent that discharges through a generally forward-directed louver 6410, and there may be a rearwardly-discharging vent that discharges through a generally rearward-directed louver 6420. Furthermore, there may be a number of approximately vertically downward directed vents discharging through respective louvers 6430. FIG. 5 shows air flow patterns describing that all of these discharges come from plenum 6490, which is supplied by four blowers 6300. It can be understood that there might be more mixing of air inside plenum 6490 than is illustrated by the simple airflow arrows indicated.

As illustrated, there are four generally downwardly-discharging vents, each approximately corresponding in location to one of the blowers 6300. They may be referred to (FIGS. 8-10A) as more-forward downward-directed louvers 6430A (two of them as illustrated) and more-rearward downward-directed louvers 6430B (two of them as illustrated). It is also possible that such downward-directed louvers 6430 could be combined into a smaller number of such louvers or even just one such louver. The various downward-directed louvers could be either identical to each other or different from each other.

Referring now to FIGS. 9-11B, in an embodiment of the invention, as illustrated, louvers 6400 may comprise some vanes 6450 that are aligned with an axis of the louver 6400 (which may be referred to as straight vanes) and there may be other vanes 6460 that are angled with respect to an axis of the louver 6400. The axis of the louver 6400 may be considered to be defined by the frame of the louver 6400. In an embodiment of the invention, as illustrated, the louver 6400 may have two vanes 6450 that are aligned with an axis of the louver 6400 and there may be three vanes 6460 that are angled with respect to an axis of the louver 6400. However, it can be understood that other respective numbers of vanes and other designs are also possible. It is further possible that some of the vanes are at one angle and others of the vanes are at a different angle, with respect to the axis of the louver 6400. One of the angles might coincide with the axis of the louver 6400 (as defined by the frame of the louver), as illustrated, but alternatively, it is possible that none of the vane angles coincides with the axis of the louver 6400.

The arrangement of such louvers and vanes to achieve a desired airflow pattern is further illustrated in FIGS. 8-11B. For example, air that is discharged through forward directed louver 6410 may be spread out so that the portion of that flow exiting through the straight vanes 6450 and flowing closer to the ceiling proceeds in a generally horizontal direction, while air that is discharged through the same louver 6410 through the angled vanes 6460 flows in a partly-forward-partly-downward direction. The same is true for rearward directed louver 6420. In regard to vertically (downwardly) directed louvers 6430A, 6430B, the vanes closest to the exterior of the vehicle may be straight vanes 6450, while vanes 6460 closer to the centerline or central aisle of the vehicle may be angled so as to direct some flow partly downward and partly toward the central aisle of the vehicle.

Although the vanes are illustrated as being straight, curved vanes are also possible.

Blowers

Blowers 6300 are illustrated in FIGS. 6A-8 and 13-16. If the air treatment unit 6000 comprises a blower(s) 6300, the blower(s) 6300 may have an axis of rotation 6302 that at least roughly coincides with the front-back direction of the vehicle. It is possible that a motor 6390 may have a shaft extending out of both ends and may have an individual blower impeller attached to each end of the shaft. Each blower impeller may itself be elongated along the shaft direction. As illustrated, there may be two motors 6390 with each motor 6390 having a blower 6300 at each end of the shaft of the motor 6390, thereby resulting in four blowers 6300 on two motors 6390. The axial dimension of individual blower impellers and the use of two blowers 6300 with an individual motor 6390, and the use of two motors 6300, may contribute to the overall elongated proportions of the air treatment unit 6000 as illustrated in FIG. 6B. Other configurations are also possible. Any desired number of blowers 6300 and motors 6390 may be provided.

Filtration

Figure 13:
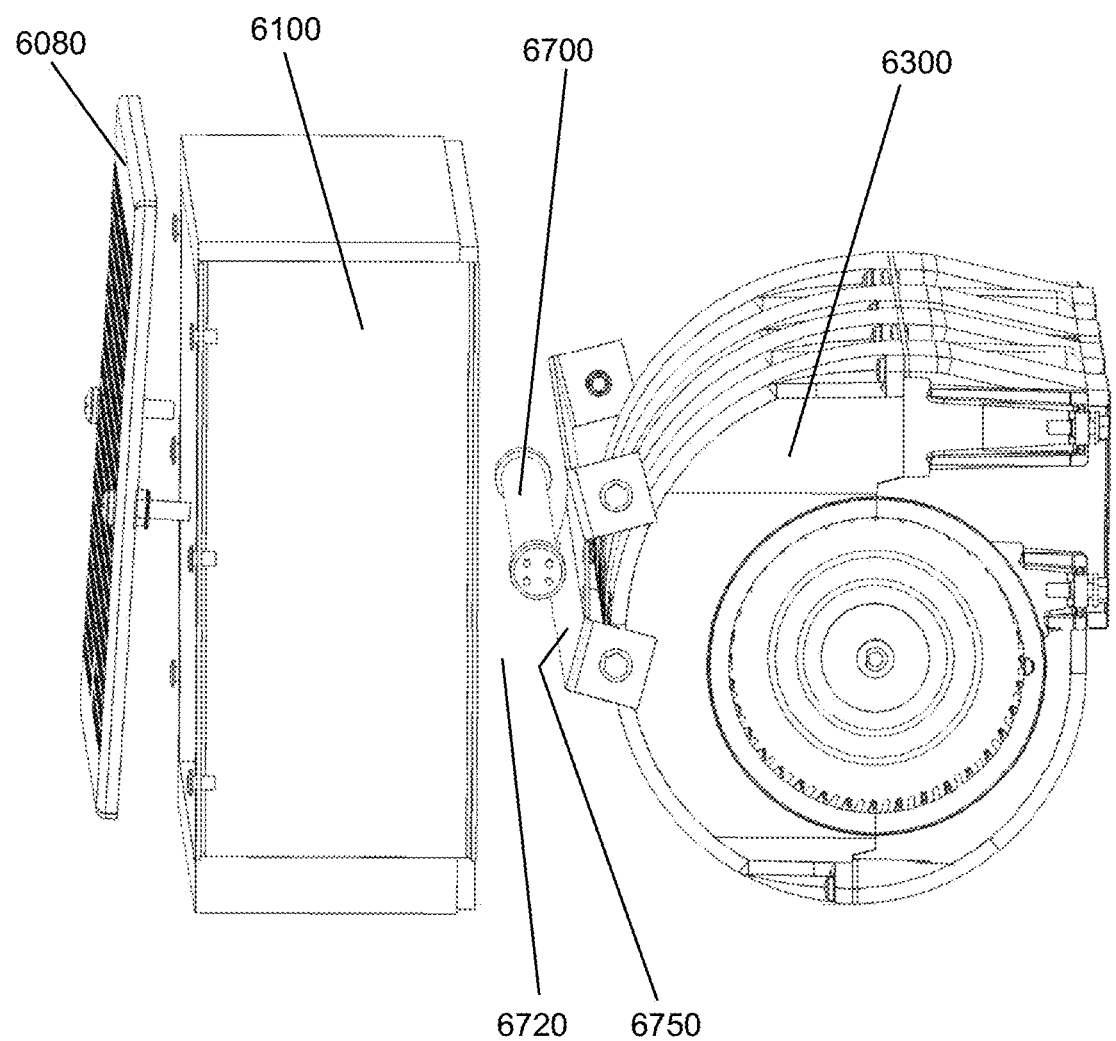
FIG. 13 shows the placement of the Ultraviolet light source, a shield, and the blowers.
Figure 14:
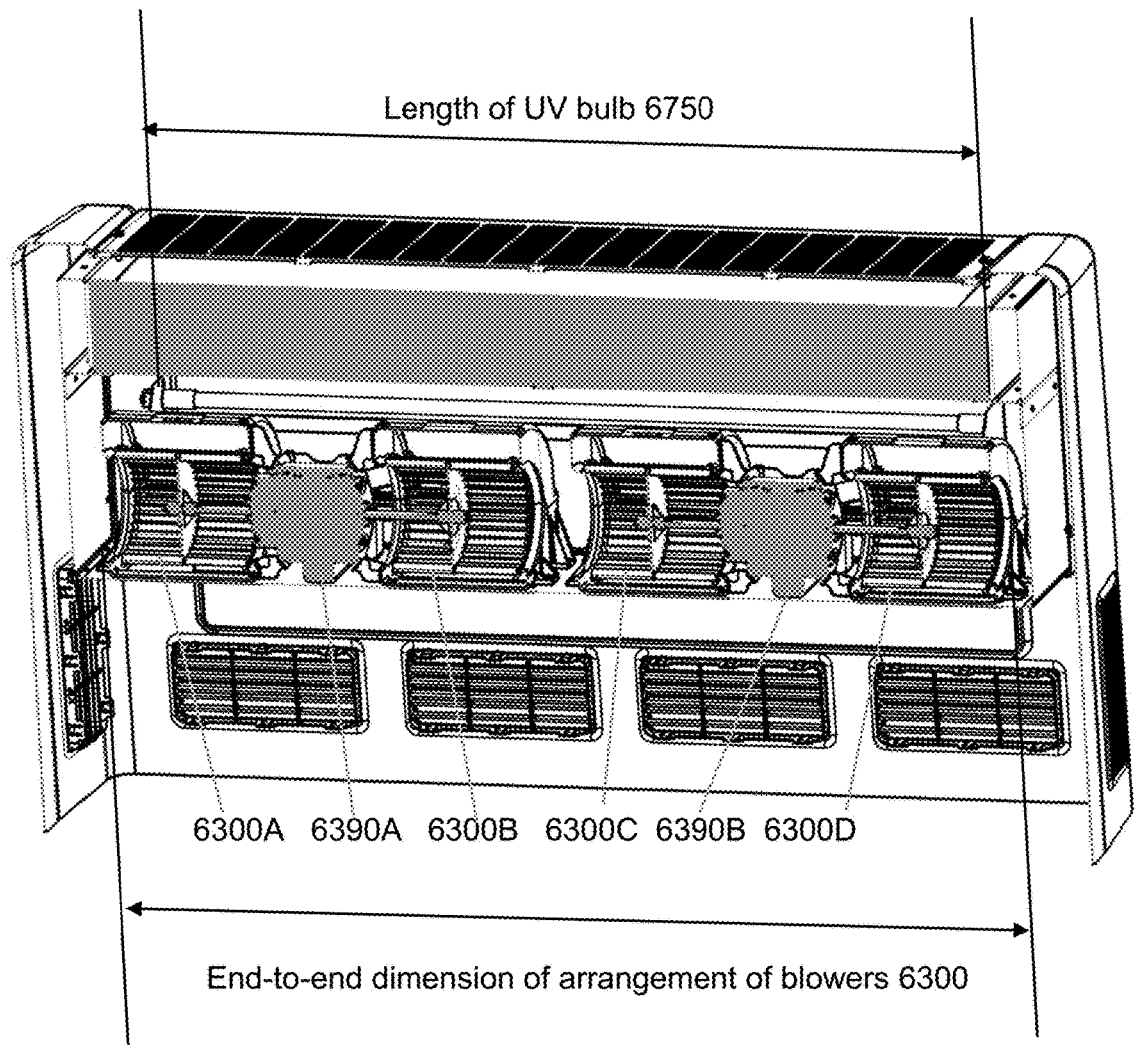
FIG. 14 is another view, in section, showing the placement of the Ultraviolet light source and nearby components.
Figure 15:
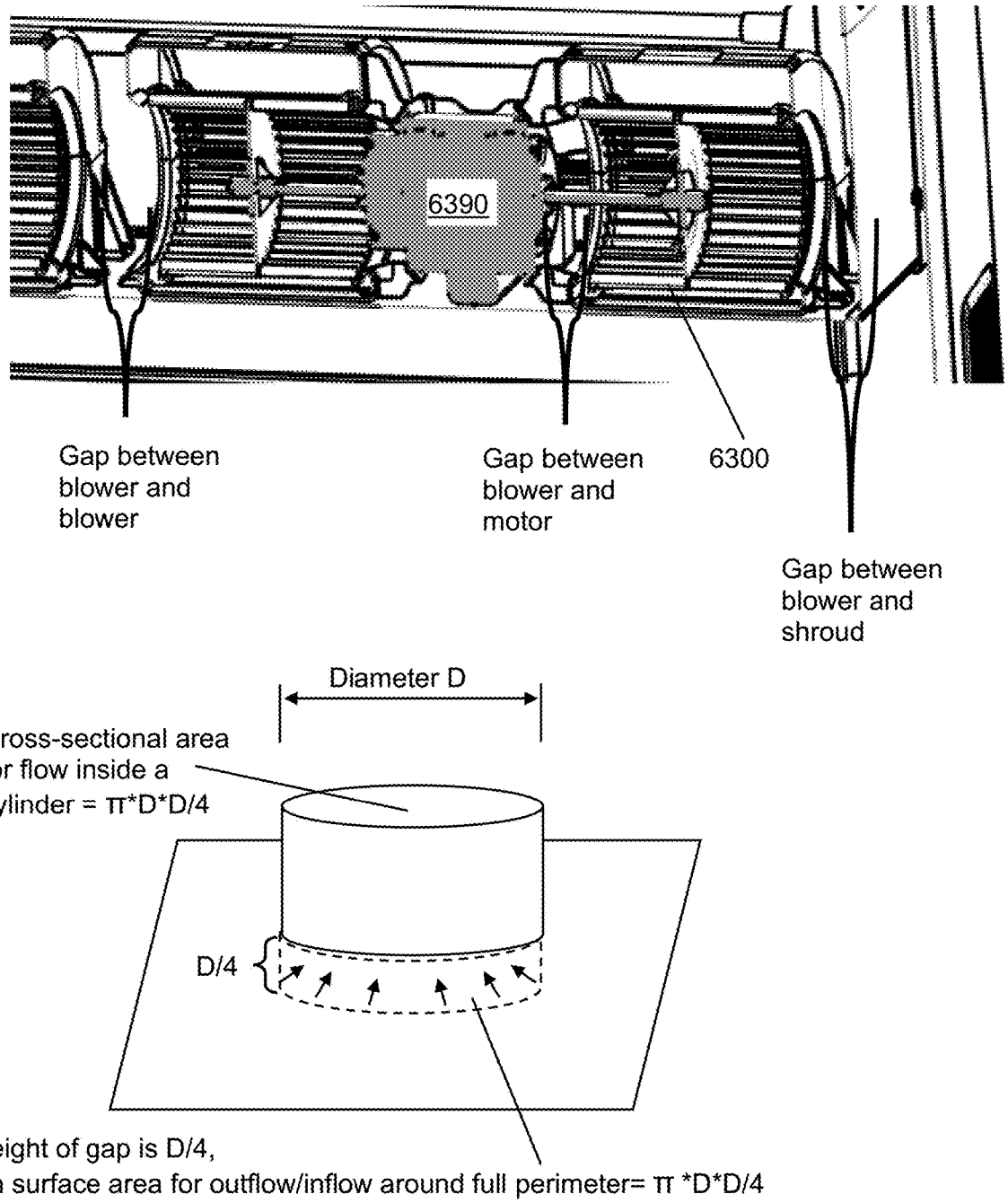
FIG. 15 shows geometric relationships among the Ultraviolet light source, the blowers and certain gap distances.

One mode of treating air is filtration of the air. Representative filters and related components are illustrated in FIG. 12A-C. FIG. 12A shows the grille 6080, FIG. 12B is a photograph of the pre-filter 6090, and FIG. 12C is a photograph of the HEPA filter 6100, also including a gasket 6102 associated with the filter 6100. FIG. 13 shows a general arrangement of major components including grille 6080, and a HEPA (High Efficiency Particulate Air) filter 6100. The COVID-19 virus, as an individual entity, is known to have a size of approximately 100 nanometers, which is smaller than the size of most bacteria. Also, the virus is known to be transmitted when attached to droplets or particulates having a size larger than that. The droplets or particulates may be emitted by people during coughing or sneezing, during ordinary exhalation of air, during shouting or singing, etc. Droplets may be in the size range of 1 to 5 microns.

The quantity Minimum Efficiency Reporting Value, commonly known as MERV, is a measurement scale designed by the American Society of Heating, Refrigerating and Air-Conditioning Engineers (ASHRAE) to report the effectiveness of air filters. The MERV value can range from 1 to 16. Higher MERV values correspond to a greater percentage of particles captured on each pass, with a MERV 16 filter capturing more than 95% of particles over the full range. The scale is designed to represent the worst-case performance of a filter when dealing with particles in the range of 0.3 to 10 micrometers. It is found that less obstructive, medium-efficiency filters of MERV 7 to 13 are almost as effective as true HEPA filters at removing allergens, while having much lower associated system and operating costs [Wikipedia]. Following is a rough indication of MERV values according to particle size. MERV 1-4 corresponds to Minimum particle size >10.0 µm. MERV 5-8 corresponds to Minimum particle size 10.0-3.0 µm. MERV 9-12 corresponds to Minimum particle size 3.0-1.0 µm. MERV 13-16 corresponds to Minimum particle size 1.0-0.3 µm. This is described in Table 1.

A grille 6080 (having openings that are even more coarse than the pores of the pre-filter 6190) may also be used upstream of the pre-filter 6090.

Pre-Filter

The pre-filter 6090 may be located upstream of the HEPA filter 6100, and may be coarser or less selective than the HEPA filter 6100. The pre-filter may be capable of removing some relatively larger particles from the airstream passing through it, thereby relieving the HEPA filter 6100 of the need to capture those particles. The pre-filter 6090 can be washable and reusable. Alternatively, the pre-filter 6190 could be replaceable intended for replacement after being in use for a certain period of time. This pre-filter 6190 may be made of aluminum mesh/screen and as such, would be fire-rated as well as washable and reusable. The pre-filter 6090 is shown as being surrounded by a frame, and the frame may be suitable to interface with the housing or some other component of the air treatment system. The pre-filter 6090 may have a MERV rating of about 4. MERV ratings are described in Table 1 (from American Society of Heating Refrigerating and Air Conditioning Engineers).

TABLE 1

| MERV Value | The filter will trap Average Particle Size Efficiency 0.3-1.0 micron | The filter will trap Average Particle Size Efficiency 1.0-3.0 micron | The filter will trap Average Particle Size Efficiency 3.0-10.0 micron | Types of things these filters will trap |
|---|---|---|---|---|
| MERV 1 | — | — | Less than 20% | Pollen, dust mites, |
| MERV 2 | — | — | Less than 20% | standing dust, spray |
| MERV 3 | — | — | Less than 20% | paint dust, carpet |
| MERV 4 | — | — | Less than 20% | fibers |
| MERV 5 | — | — | 20%-34% | Mold spores, hair |
| MERV 6 | — | — | 35%-49% | spray, fabric |
| MERV 7 | — | — | 50%-69% | protector, cement |
| MERV 8 | — | — | 70%-85% | dust |
| MERV 9 | — | Less than 50% | 85% or better | Humidifier dust, |
| MERV 10 | — | 50%-64% | 85% or better | lead dust, auto |

TABLE 1-continued

| MERV Value | The filter will trap Average Particle Size Efficiency 0.3-1.0 micron | The filter will trap Average Particle Size Efficiency 1.0-3.0 micron | The filter will trap Average Particle Size Efficiency 3.0-10.0 micron | Types of things these filters will trap |
|---|---|---|---|---|
| MERV 11 | — | 65%-79% | 85% or better | emissions, milled flour |
| MERV 12 | — | 80%-89% | 90% or better | Bacteria, most tobacco smoke, proplet nuclei (sneeze) <0.30 pm particle size; virus (unattached), carbon dust, all combustion smoke |
| MERV 13 | Less than 75% | 90% or better | 90% or better | |
| MERV 14 | 75%-84% | 90% or better | 90% or better | |
| MERV 15 | 85%-94% | 90% or better | 90% or better | |
| MERV 16 | 95% or better | 90% or better | 90% or better | |
| MERV 17-20 | n/a | n/a | n/a | |

HEPA Filter

Referring now to the HEPA filter 6100, commercially available HEPA filters can be made with ratings of particulate removal down to a particle size of 0.3 microns. It is believed that such HEPA filters 6100 can also remove particles that are even smaller than that size, with a removal performance that is imperfect but still useful. Particle removal is strongly influenced by the size of pores or inter-fiber spaces in such filters. It is believed that the HEPA filter 6100 will be used in conjunction with a maintenance schedule that calls for the HEPA filter 6100 to be removed and replaced after a designated period of time in service. However, other options (such as being washable) may also be suitable.

A typical HEPA filter 6100 comprises a filtration medium, which may be a porous or fibrous material. The filtration media does not have significant degradation upon exposure to UV light. Often such material is pleated or corrugated. Such pleated or corrugated geometry increases the filtration area by a factor of several times, so that the filtration area is an area that is larger than the simple frontal area of the filter. A HEPA filter 6100 may also comprise a face guard on either or both of its upstream or downstream faces. The face guards may cover the region where the pleated filtration medium exists, and the face guards may have holes or pores that are significantly larger than the pores of the filtration medium. The face guards may provide mechanical protection for the filtration medium during handling etc. These components may be surrounded by a frame, which may, for example, be made of aluminum.

As a result of the consideration of vibrations due to driving, in an embodiment of the invention, the HEPA filter 6100 (or any filter herein) may be constructed with the edges of the filtration medium, even if it is pleated, being potted in a potting material. It is believed that having edges that are potted in a potting material is helpful for withstanding the vibrations experienced by a vehicle traveling on a road. It is believed that the potting is helpful for preventing the filtration material from deforming due to the vibrations and for preventing the formation of possible gaps at edges of the filtration material, which might allow passage therethrough of pathogens or contaminants. The potting material may be a material that can be used in liquid or flowable form, and can then harden. In its hardened condition, the potting material may grasp and form a seal at the edges of the filtration medium. A common potting material is urethane. Other potting materials are also possible.

The HEPA filter 6100 may be surrounded by a frame, which may be made of metal and may have a U-shaped cross-sectional shape. The potting material or adhesive material may exist within the interior of the U-shaped cross-sectional shape of the frame. The potting material or adhesive material may be, for example, urethane. Also existing within the interior of the U-shaped cross-sectional shape of the frame may be glue bead separators for keeping pleats apart in their proper position, and these separators may also be polymeric and subject to degradation from UV exposure. In an embodiment, any or all of these may be shielded at least to some extent from UV illumination by the frame, particularly the legs of the frame, and also may be shielded by face guards if face guards are present.

The frame of the filter 6100, in turn, may interface with the body of the air treatment unit through a gasket or seal. The gasket may be a polymeric foam or may be or comprise a deformable polymer such as rubber. Such gasket may be located at a relatively exterior part of the HEPA filter on a flat externally-facing surface of the frame.

In an embodiment of the invention, the HEPA filter 6100 may have a thickness, along the direction of airflow through the filter, of approximately 3.5 inches. In its face directions (perpendicular to the direction of airflow through the filter), the HEPA filter 6100 may have dimensions such as 9 inches by 36 inches.

Ultraviolet Light

In general, viruses can be killed or inactivated by exposure to ultraviolet light. It is believed that ultraviolet light disrupts the RNA of the virus, which is an effect that also occurs for other microorganisms when they are exposed to UV light. Therefore, in embodiments of the invention, the air treatment system 6000 can also comprise a UV light source 6700. The combination of filtration and UV light can provide capture of many contaminants in combination with killing/inactivation of contaminants that might or might not be captured.

The term ultraviolet light may be understood to include a range of wavelengths of electromagnetic radiation. It is conventionally considered that there are ranges or bands of ultraviolet light designated as UVA, UVB and UVC, with UVA considered to be 400 nm to 320 nm; UVB considered to be 320 nm to 280 nm; and UVC considered to be 280 nm to 200 nm. UVA and UVB are considered ineffective against microorganisms. UVC is considered effective against microorganisms while it also is dangerous to humans. A commonly used wavelength of UVC light is 254 nm, which is available from tubes that resemble conventional fluorescent light tubes for interior lighting, except that the fluorescent coating of conventional fluorescent light tubes is different or omitted. Of relatively recent interest, there is a further particular subset of UVC light called far-UVC having a wavelength ranging from 207 nm to 222 nm. Far-UVC is considered to be effective against pathogens while also being relatively safe for human exposure. Another category called far-UV light is considered to be UV light having a wavelength in the range of 200 nm to 122 nm or 100 nm. Far-UV light is able to cause physical destruction of viral, bacterial, and fungal contaminants much faster than light in the UV-C range. Far-UV is sometimes also called vacuum UV, because of its ability to travel through vacuum while having only limited ability to travel through air.

In another aspect of ultraviolet light, it is believed that, in general, longer-wavelength UV light does not cause formation of ozone from oxygen in air, while shorter-wavelength UV light causes the formation of a small amount of ozone. The question of whether there is net production of ozone, at a particular wavelength of UV light, is believed to depend on the comparison or balance between the rate of formation of ozone and the rate of decomposition of ozone. Ozone may attack microorganisms by a mechanism different from the mechanism by which ultraviolet light attacks microorganisms. Ozone may be undesirable for release into the occupied region of the vehicle if passengers are present, but the formation of a small amount of ozone may be useful for disinfecting either air or surfaces inside the air treatment system.

The air treatment region of the air treatment system may be provided with an ultraviolet light source 6700 directed at least at the air that is passing through the air treatment region. Air that is passing through the air treatment region may have an exposure time (duration of exposure of the air to ultraviolet light as the air passes through the air treatment region) that is determined by the flowrate of air, cross-sectional dimensions of the air treatment region, the dimension of illuminated region along the flow direction, and other parameters. Such exposure time duration may be selected, in conjunction with dosage or illumination parameters of the UV light, so as to provide UV exposure properties that are useful for killing or inactivating pathogens that may be suspended in the air passing through the UV exposure region 6720.

It can be understood that in the air treatment region, the UV light source 6700 emits rays that travel directly from the UV light source 6700, pass through the air being treated, and strike an interior surface of a component or boundary of the air treatment region. Upon striking such surface, the rays may reflect and may repeat still further reflections. The reflections from the various surfaces have many possibilities and may create a diffuse illumination within the air treatment region. Thus, components within the air treatment region may be exposed to both direct and diffuse illumination of UV light.

In an embodiment of the invention, the ultraviolet light source 6700 may be a bulb or tube that resembles a conventional tubular fluorescent light bulb, but contains less or none of the substance that in a conventional fluorescent light bulb converts ultraviolet light to visible light. The UV light source 6700 may deliver ultraviolet light in the spectral range of UVC, such as at a wavelength of 254 nm. In an embodiment of the invention, the UV light source 6700 may be a tubular bulb that is substantially straight. Such bulb may extend generally parallel to the axis of rotation 6302 of the blowers 6300, and may extend along most of the long dimension of the air treatment system 6000. Another alternative is a J-shaped UV light source made by Sanuvox (Montreal, Canada), such as their model VP900GX.

The UV bulb 6700 may be powered by a ballast that is operable with input electrical supply of approximately 12 VDC, which is the electrical supply that is typically available in motor vehicles, or 24 VDC as may be available on transit buses and motor coaches, or some other voltage if desired. In an embodiment of the invention, it also is possible that UV light can be produced by Light Emitting Diodes (LEDs). Combinations of such sources are also possible.

Shielding and Protection from UV Light

Humans should not be exposed to the ultraviolet light that is emitted inside the air treatment unit 6000. Accordingly, the air treatment unit 6000 in general, and the UV exposure region 6720 in particular, may be designed such that no significant amount of ultraviolet light escapes from the air treatment region to the passenger region of the vehicle. This can be accomplished, for example, by eliminating line-of-sight pathways, such as cracks and straight ducts, through which light could travel from the UV exposure region 6720 to the rest of the vehicle.

Yet another consideration is that upon exposure to UV light, certain materials can suffer degradation or damage in their mechanical properties or other properties. This is particularly true for certain polymers. This can be a consideration for the filtration medium itself, for potting material if used, for a possible HEPA filter face guard that covers the filtration medium, and for miscellaneous structural components that may be made of polymers. For example, components of the blower either may be made of UV-resistant material or may be shielded from UV light within the air treatment region, or both.

If the housings of the blowers 6300 are made of a material, such as polymer, that is susceptible to damage from UV light, there may be provided a shield 6750 that shields such components from direct exposure to UV light, at least to some extent, and also shields them from diffuse UV light at least to some extent. Such shield 6750 may, for example, be made of metal. Such a shield 6750 may generally be located between the UV light source 6700 and the housing of blower 6300.

The HEPA filter 6100 may have a construction such that it is surrounded by a frame which may (in cross-section) be a U-shaped frame that may have sharp corners. The potting or adhesive may be hidden inside the frame and therefore may be at least somewhat shielded from UV illumination by the legs of the U-shaped frame. It is possible that if the HEPA filter 6100 contains a face guard, the face guard may provide some protection of more-internal components, such as the potting/adhesive, against UV light. Even if these protections against exposure to UV light are not perfect, they are likely to substantially reduce the UV exposure of the potting material, such as by 90% compared to what would occur in the absence of such features.

The shield 6750 may serve to keep the UV light away from the housings of blowers 6300. The shield 6750 may be made of metal, for example. The air treatment unit 6000 may be designed such that the UV light source 6700 is at least 0.25 inch or 0.5 inch away from any other surfaces.

Overall System Parameters and Modes of Operation

In an embodiment of the invention, the air treatment system 6000 may have parameters such as the following:
  Airflow: 400 cubic feet/minute
  Electrical usage of motors for blowers: 22 Amps at 14.2 VDC
  Air treatment unit external dimensions: approximately 10.48 inches by 23.87 inches by 42.12 inches.

Pre-Filter 6090: Aluminum mesh, mounted in a frame

HEPA filter 6100: true 99.99% efficiency for particles of 0.3 microns size, at an air flow face velocity of 100 ft/min HEPA filter thickness along the flow direction: approximately 3.5 inches. Filtration medium may be pleated. Pleat depth 70 mm (2.75 inches). Resistance: 0.38 inch water gage at 100 ft/minute face velocity For a typical application, in which the vehicle interior volume may be approximately 2,000 cubic feet and the airflow of a single air treatment unit 6000 may be 400 cfm (which is 24,000 cubic feet per hour). Thus, if a single air treatment unit 6000 were operating, there would be 12 air changes per hour, which is believed to be appropriate according to US government health guidelines. If there are two such units in a vehicle, there would be twice as much airflow and there can be expected to be 24 air changes per hour.

HEPA filter construction: Filter media: Micro glass paper. Frame material: anodized extruded aluminum. Sealant material: fire retardant polyurethane. Protective grille: Expanded metal painted white both sides. Gasket material: Neoprene downstream.

It is believed that the pre-filter 6090 would have a MERV rating of approximately 4. It is believed that the HEPA filter 6100 would have a MERV rating of better than 16. The particle size retention of the HEPA filter 6100 is rated at 99.99% of 0.3-micron particles, at a face velocity of 100 feet/minute. In embodiments of the invention, the operating conditions may be a face velocity of approximately double that value, so the fraction of particles retained would be slightly reduced, but it is believed that this would be more than offset by the increased flowrate and number of air changes per hour in the space that is being treated.

Electrical and Optical Parameters

The UV light source 6700 may be suitable to operate from an electrical supply that is Direct Current of the vehicle power system, which typically is 12 VDC or 14.2 VDC. The described apparatus can produce UV light at a wavelength of 254 nm, which is within the UVC range and is favorable for killing/inactivating microorganisms of interest.

In an embodiment of the invention, it is possible to use a ballast that is part number 10-1085 from Atlantic Ultraviolet Corporation (Hauppauge, N.Y.), operating from a supply voltage of 12 Volts. This ballast can drive the Atlantic Ultraviolet lamp G36T5L/4 lamp part number #05-1380-R or #05-1382-R. This lamp emits Ultraviolet light at a wavelength of 254 nanometers, which is a commonly used wavelength that is in the UVC range. This is considered to be a low ozone type of UV light source.

It can be noted that the nature of certain viruses or microorganisms, in combination with the available intensity of UV from certain UV sources, is such that the duration of exposure required to fully kill/inactivate the microorganism might be many seconds or some number of minutes. For typical operating parameters of air flows and velocities through the described air treatment system, it is likely the residence time of air inside the UV exposure region 6720 (being exposed to UV light) during one pass through the air treatment system is only several seconds at most. This duration of time may not be sufficient to kill/inactivate the entire assumed load of virus or microorganisms. Nevertheless, it can be expected that over a period of operation of air treatment system 6000, the air will flow through the air treatment system 6000 multiple times and therefore will accumulate extended exposure to UV light enough to have a useful effect in killing/inactivating viruses or microorganisms. The number of passes of air through the air treatment system 6000 appropriate to kill/inactivate microorganisms by UV light may be different from the number of passes of air through the air treatment system 6000 appropriate to achieve removal of viruses/microorganisms from the air by filtration. It can be noted that both modes of treatment (UV exposure and filtration) have useful roles in disinfecting the air.

Additional Features Regarding Controls and Wavelengths of UV

In an embodiment of the invention, the air treatment system 6000 could have more than one UV light source 6700 such as to provide various different wavelengths of UV light, or a given UV light source could be operated in different ways so as to provide various different wavelengths of light. As described, different wavelengths of UV light have different killing/inactivating effects on different microorganisms. Additionally, and more particularly, some wavelengths of UV light do not create ozone while other wavelengths of UV light do create ozone, and ozone has its own disinfecting effect which may operate on microorganisms in addition to or differently from the direct effect of UV light. For example, it is possible to purchase UV light bulbs of two different types that operate using identical sockets and electrical supply, except that one type produces ozone and the other type does not produce ozone. If the air treatment apparatus contains two UV light bulbs, one of which produces ozone and the other of which does not, it is possible to decide whether to produce ozone or not, simply by deciding which UV light bulb is electrically powered.

In an embodiment of the invention, there may be provided a safety feature such that, if a person disassembles the air treatment system, for normal service or repair, it becomes impossible for the UV light source to be illuminated or powered. This feature can take the form of a microswitch or an interlock that engages with or senses the position or presence of the shroud 6070 or any other component that is involved in providing access to internal components of air treatment system 6000. The logic could be such that if the shroud 6070 or filter 6100 or other component is removed from the air treatment system, the supply of electrical power to the Ultraviolet light source is shut off or disconnected. This can be a safety feature for the eyes and skin of repair people or anyone else who disassembles the system, and it also can be a safety feature regarding voltage that may be present within the ballast of the lighting system.

Prevention of Escape of Ultraviolet Light into the Vehicle Space

In an embodiment of the invention, Ultraviolet light may be produced inside the UV exposure region 6720 of the air treatment system 6000, and this production of UV light may occur while occupants are in the vehicle. Because ultraviolet light is hazardous to humans, it is important to confine the UV light within the air treatment region and not let it escape into the vehicle space even though entrances and exits are provided for air to enter into and exit from the air treatment region.

Similar to the situation with visible light, UV light can travel in any of several ways. It could travel in a straight ray from its source to an exit path. This is a relatively simple mechanism, and such escape of UV light can be prevented by any solid object. In an embodiment of the invention, the UV light is produced by a tubular bulb that is fairly long relative to its diameter. It can be approximated that the direct rays of UV light are emitted generally radially from the tubular bulb. Accordingly, escape of these rays can be prevented by blocking any direct line-of-sight path from the UV light source to any opening that connects with the occupant space of the vehicle. This is a first step toward preventing such escape of UV light.

In an embodiment of the invention, it can be seen that in regard to the route for intake of air into the air treatment region, the HEPA filter 6100 provides good blockage of UV light. The HEPA filter 6100 has pores that are sufficiently small and sufficiently numerous along the direction of travel through the filter, so that it is unlikely that any significant amount of UV light can pass through the HEPA filter 6100. In regard to the discharge route of air through the blowers 6300 and plenum, first of all, there may be provided a shield 6750 near the UV light source 6700. The shield 6750 may extend in an axial direction for at least as long as the length of UV light bulb 6700. In a cross-section taken through the UV light bulb and the shield 6750, the shield 6750 may block transmission of UV light in certain directions such that the intake of the blower 6300 is entirely in the shadow of the shield 6750.

Direct shine is not the only possible route of escape of UV light. It also is possible for UV light to reflect off of solid surfaces that are exposed to UV light, i.e., surfaces that exist either within or at the boundary of the air treatment region. The more well-defined form of reflection is specular reflection, such as reflection from a mirror. In such reflection, with respect to a flat surface or more generally the local tangent to a surface, the reflection is governed by the angle of incidence and the angle of reflection being equal. This type of escape of light can be prevented by drawing various rays emanating in various directions from the UV bulb 6700 and reflecting from a surface, and seeing if any of them can reach an opening or exit by a path that involves specular reflection. Such escape of UV light can be defeated, in general, by blocking and shielding similarly to what is done to defeat direct shine, but with the blocking shielding being more extensive and blocking more paths or being more convoluted than what is done simply to defeat direct shine. It also is possible that some energy of the UV light is lost at each reflection.

Yet another form of reflection is diffuse reflection. Diffuse reflection is reflection in which the angle of reflection is different from the angle of incidence, with a typical example being a surface that is not truly flat or smooth but rather is locally rough. The local irregularities of the roughness introduce unpredictability as to the geometric path for any particular reflection of a ray of light. Such escape of UV light can be defeated, in general, by blocking and shielding similarly to what is done to defeat both direct shine and specular reflection, but with the blocking shielding being still more extensive and blocking more paths or being more convoluted than what is done simply to defeat both direct shine and specular reflection.

In general, for all of these possible mechanisms of escape of UV light from the air treatment region 6720, it is favorable to have an air exit path that involves corners and changes of direction, as well as solid objects.

Yet another strategy that can be used to prevent escape of UV light is to choose surface properties of UV-exposed solid surfaces in the air treatment region 6720 such that the surfaces are non-reflective to UV light.

In an embodiment of the invention, air may be moved by a centrifugal blower 6300. The centrifugal blower 6300 may have a housing and, inside the housing, an impeller that is rotatable around an axis of rotation 6302 and that extends generally along the axis of rotation 6302. The impeller may have a central region that is somewhat open for intake of fluid along the direction of the axis of rotation 6302. The fluid is then flung outward by the action of the blades of the rotating impeller, the blades being located in the outer region of the impeller, and the fluid then exits the housing through an outlet that is at a location radially outward of the impeller. Generally, there is one outlet at one location at the circumference of the housing, and the outlet has a direction that is somewhat tangential to the rotation of the impeller.

In an embodiment of the invention, the exit path for air may involve four blowers 6300 and a plenum 6490 downstream of the blowers 6300. More specifically, in an embodiment of the invention as illustrated, there may be two motors 6390, which may be mounted with their axes of rotation aligning with each other. For each of these motors 6390, the shafts of these motors 6390 may extend outward in both directions from the motor 6390, and the shaft may be sufficiently long so that both ends of each shaft may hold the rotor (impeller) of a blower 6300. Thus, there may be in sequence the following along the long direction of the air treatment system 6000: the shroud 6070 or a flat solid; a gap; the first blower 6300A; the first motor 6390A; the second blower 6300B; a gap; the third blower 6300C; the second motor 6390B; the fourth blower 6300D; a gap; and the shroud 6070 or flat solid. This is illustrated in FIGS. 7, 8, 14, 15, 16.

Given the general construction of blowers as described, it may be considered that a possible path for shine-through of UV light could be for light to enter in a diagonal path that passes through the axially-oriented intake of the blower, and then finds a path to the outlet of the blower. The light could, in general, be any type of light i.e., direct illumination, specular reflection or diffuse reflection. It can be noted that the blades of the impeller might not overlap with adjacent blades sufficiently to completely block shine-through.

Figure 16:
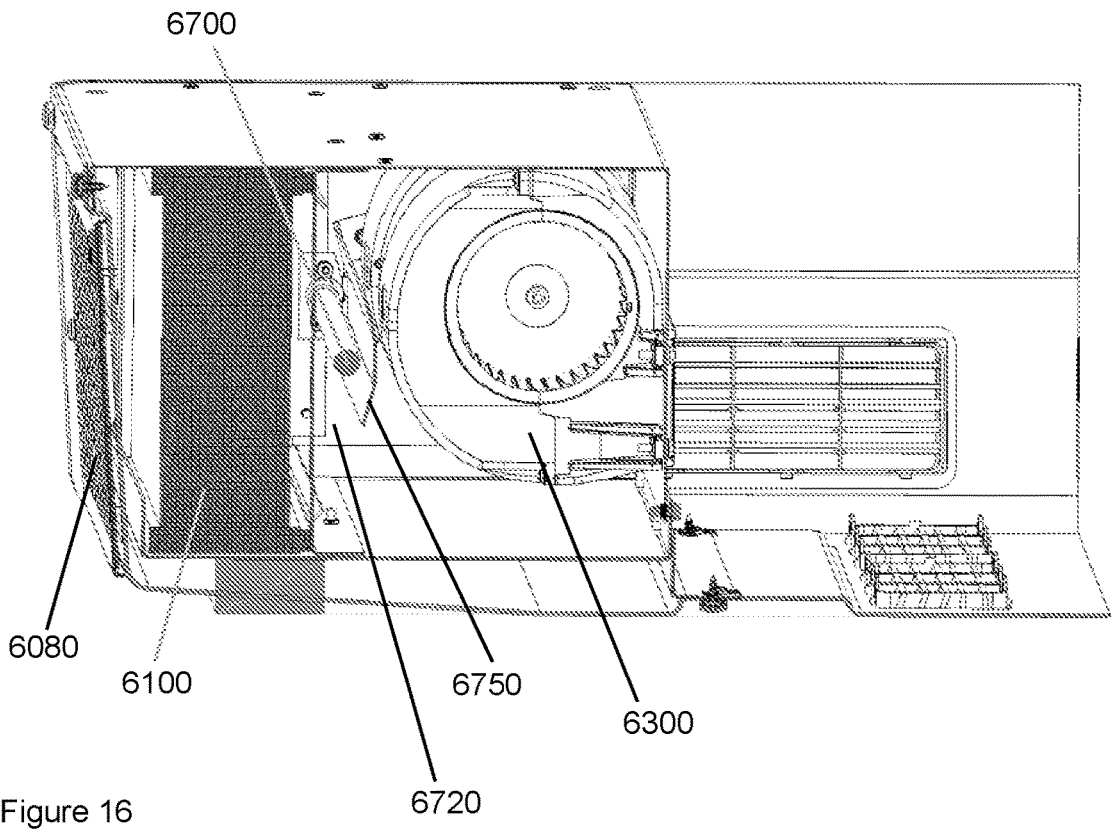
FIG. 16 shows positioning of the Ultraviolet light source and the shield.
Figure 17:
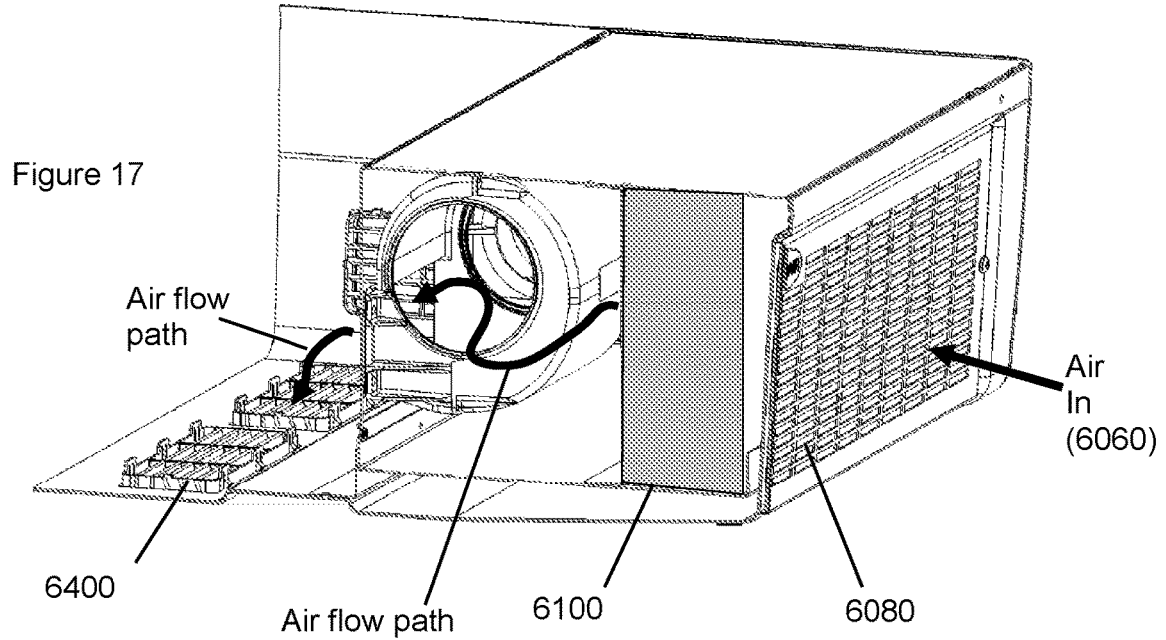
FIG. 17 shows flow patterns inside the air treatment unit.
Figure 18:
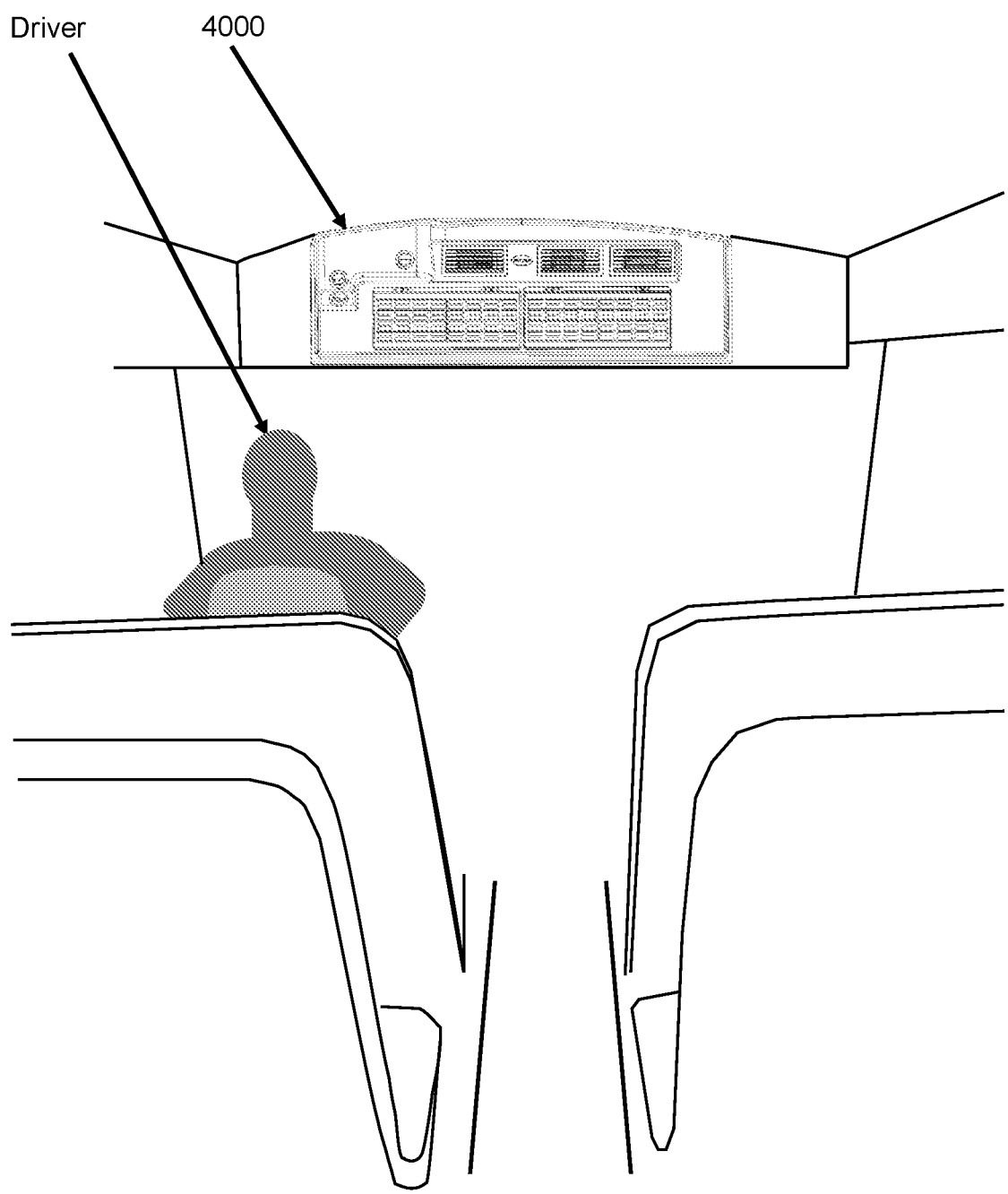
FIG. 18 shows, for another embodiment of the invention, a location of an air treatment unit at a front of a vehicle, and a corresponding airflow pattern in the interior of the vehicle.
Figure 19:
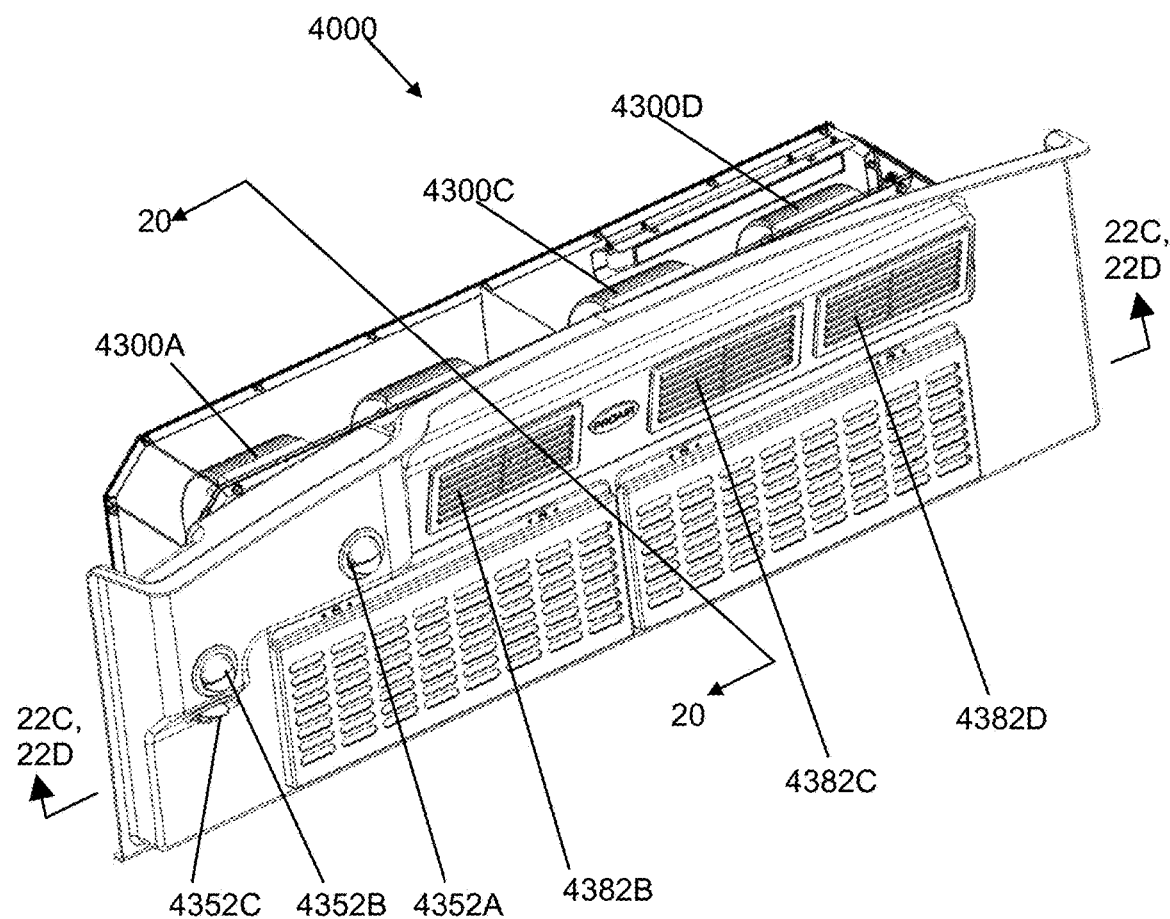
FIG. 19 shows the front panel and various external features and components (with a rear housing omitted for clarity of illustration).
Figure 20:
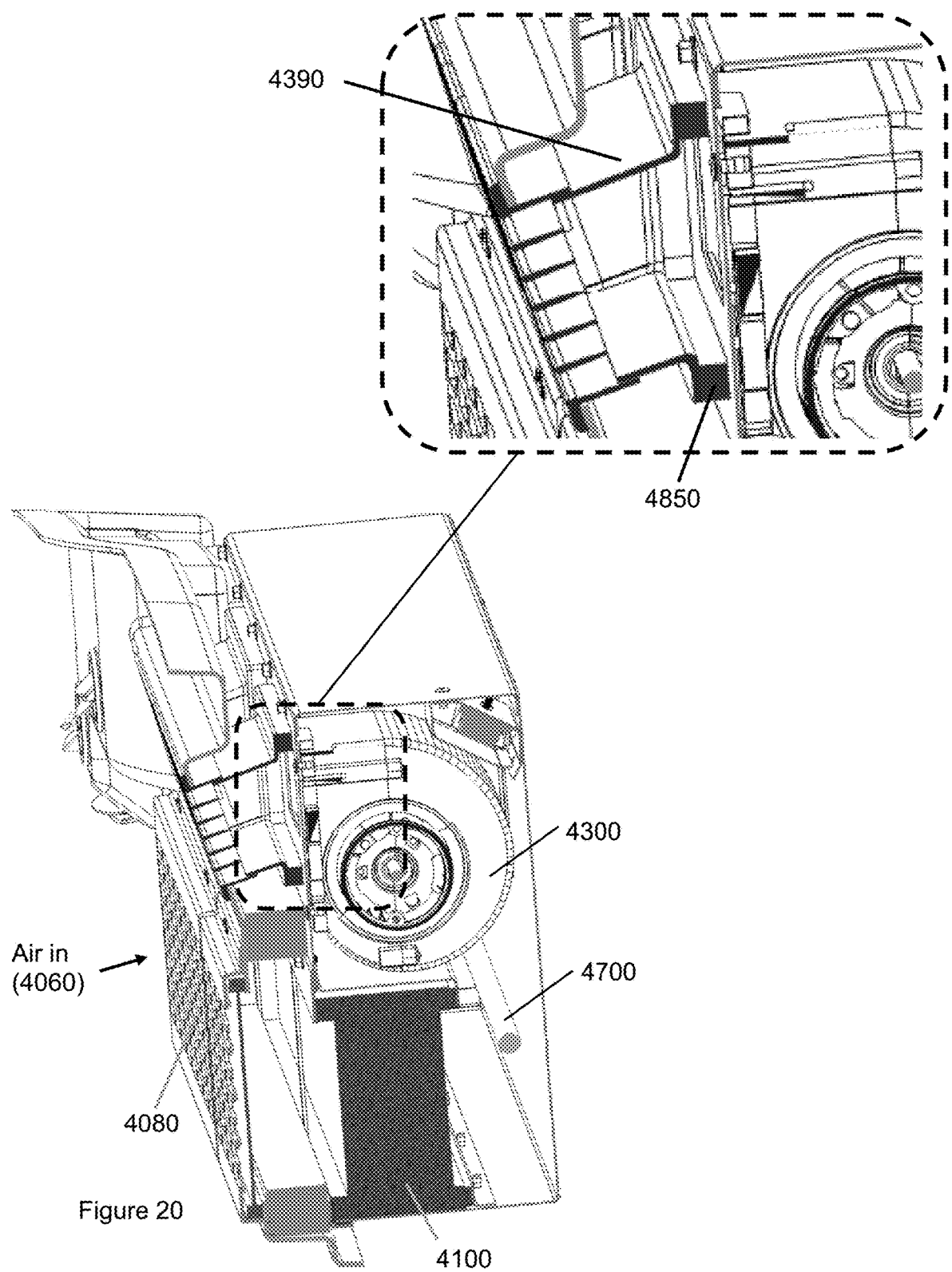
FIG. 20 shows a cross-section.
Figure 21:
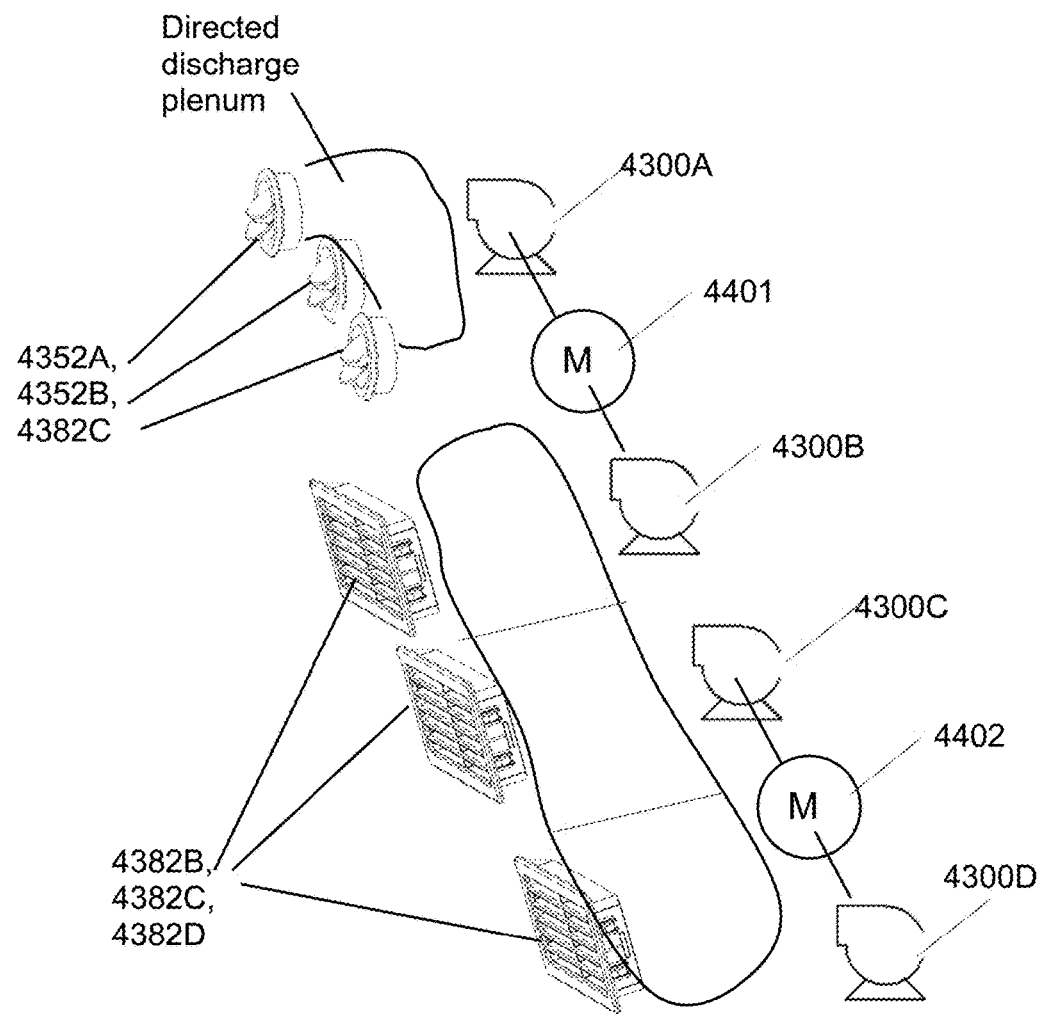
FIG. 21 shows a schematic illustration of placement and flow relationships for a plurality of blowers, a bulk discharge plenum, a directed discharge plenum, and various louvers.

In an embodiment of the invention, a design feature to defeat shine-through may be that the shield 6750 near the UV light source 6700 may be designed and dimensioned such that direct shine cannot reach the impeller intake in the view shown in FIG. 16. The limit of direct shine may be defined by a straight ray from the UV bulb 6700 passing by the extreme corners of the shield 6750. As illustrated, the intake of the blower 6300 is not in that region of direct shine. This geometry can also be helpful for also defeating indirect shine due to reflection (either specular reflection or diffuse reflection). FIG. 17 shows the path of air through the filter and entering and exiting the housing of a blower 6300. In FIG. 17 the impeller is omitted for clarity of illustration.

In an embodiment of the invention, a feature to defeat shine-through may be that the dimensions and placement of respective parts may be chosen such that the length of the UV bulb 6700 is shorter than the distance from the extreme end of the blower 6300A at one end of the arrangement of blowers to the extreme end of the blower 6300D at the other end of the arrangement of blowers.

In an embodiment of the invention, a feature to defeat shine-through may be that the dimensions and placement of respective parts may be chosen such that the length of the shield 6750 is at least as great as the length of the UV bulb or UV light source 6700. Another feature may be that the length of the shield 6750, in the axial or lengthwise direction, is longer than is the distance from the extreme end of the blower 6300A at one end of the arrangement of blowers to the extreme end of the blower 6300D at the other end of the arrangement of blowers.

In an embodiment of the invention, a feature to defeat shine-through may be that the gap between an end blower and the nearest flat structure such as shroud 6070 may be less than half of the inside diameter of the blower housing, or less than one-quarter of the inside diameter of the blower housing, but more than one-eighth of the inside diameter of the blower housing. Im FIG. 15, it is illustrated in the geometric calculation illustration that if the separation distance is one-quarter of the blower housing inside diameter, the flow area for flow flowing radially inward all around the circumference is approximately equal to the flow area for flow flowing axially inside the bore of the impeller. This would provide that at a nominal gap dimension of one-quarter of the gap at the end of the housing, so that the gap would not be a "bottleneck" for flow, compared to the bore of the impeller. A range of gap dimension around that nominal value could be from one-eighth to one-half of the housing inside diameter. If the gap dimension is greater than one-half of the housing inside diameter, the gap would not be a flow "bottleneck," but it might be more prone than necessary to allowing "shine-through" of UV.

Similarly, in an embodiment of the invention, a feature to defeat shine-through may be that the gap between a motor and a blower that is mounted on the shaft of the motor may have values similar to those just discussed for the gap between the blower and a structure.

For a gap between a blower and a neighboring blower wheel that is on a different motor shaft, the gap serves a slightly different purpose, in that the flow flowing in the gap enters two different blowers. Thus, the gap corresponding to avoiding a bottleneck would be twice the value that would be used between a blower and a nearby flat structure. In an embodiment of the invention, a feature to defeat shine-through may be that the gap between such a blower and its neighboring blower on a different shaft may be less than the inside diameter of the blower housing, or less than half of the inside diameter of the blower housing, but more than one-quarter of the inside diameter of the blower housing.

These dimensional choices may represent an appropriate choice that allows enough space for air to flow without undue obstruction or flow resistance, while still providing good blockage against possible shine-through of UV light.

Embodiment HEPA-4

In another embodiment of the invention, which may be referred to as HEPA-4, referring now to FIGS. 18-23C, there may be provided an air treatment system 4000 that provides both a directed air flow and a bulk air flow. Such an air treatment system may, for example be suitable to install at the front of a vehicle such as a bus, possibly near the ceiling of the vehicle. The bulk air flow may be directed generally at the interior space of the vehicle. The directed air flow may, optionally, be directed at the region occupied by the driver. Air may be taken in through air intake 4060 and may then pass through a filter 4100, which may be a HEPA filter, and then may be exposed to an ultraviolet light source 4700.

In an embodiment, the air treatment system 4000 may be mounted generally at the front of the interior region of the vehicle, facing generally rearward, and the directed discharge plenum 4350 and its associated directed discharge plenum louvers 4352A, 4352B, 4352C may be closer to the vehicle driver's seat and the other discharge geometries from other blowers may be further from the driver's seat. Accordingly, the directed discharge plenum 4350 and its plurality of directed discharge plenum louvers 4352A, 4352B, 4352C may be adapted to direct air more specifically toward the driver of the vehicle, while the bulk discharge louvers 4382B, 4382C, 4382D may be adapted to direct air generally more toward the passengers than the driver.

In an embodiment, the air that is discharged from the directed discharge plenum louvers 4352A, 4352B, 4352C may be discharged at a larger velocity than the air that is discharged from the bulk discharge louvers 4382B, 4382C, 4382D.

In an embodiment of the invention, inside the air treatment system 4000 there may be provided a plurality of blowers 4300. The blowers 4300 may be centrifugal blowers as are known in the industry. Each blower 4300 may have a respective blower discharge geometry, which may, as illustrated, be generally rectangular.

In an embodiment, the various blowers 4300A, 4300B, 4300C, 4300D may be identical to each other, although they do not have to be. In an embodiment, as illustrated, the various blowers 4300 may have respective rotational axes that are generally parallel to each other. In an embodiment, as illustrated, the various blowers 4300 may all share a common rotational axis. As illustrated, the various blowers 4300 may all be mounted in a linear arrangement with each other, and their blower discharge directions may be parallel to each other.

In an embodiment, two blowers may be mounted on the shaft of a motor, with one blower each at opposite sides or ends of the motor shaft, as illustrated. For example, as illustrated, there may be four blowers 4300A, 4300B, 4300C, 4300D and two motors 4401, 4402. The various motors 4401, 4402 and blowers 4300A, 4300B, 4300C, 4300D may be identical to each other, although they do not have to be. The motors 4401, 4402 may be separately controlled and may be able to be operated in ways that are different from each other, or they could be controlled from a common source.

In an embodiment, as illustrated, the flow conditions downstream of the various blowers 4300A, 4300B, 4300C, 4300D may differ from each other. First of all, it is possible that each blower 4300 may have a respective plenum and discharge louver(s) that is substantially isolated from other plenums and other discharge louvers by a separator which may as illustrated be a foam gasket 4850. The air treatment system 4000 may comprise a directed discharge plenum 4350, such that as illustrated, one of the blowers 4300A may discharge into the directed discharge plenum 4350. The directed discharge plenum 4350, in turn, may comprise a plurality of directed discharge plenum louvers 4352A, 4352B, 4352C, as described elsewhere herein.

In an embodiment of the invention, there may also be provided bulk flow plenums 4380B, 4380C, 4380D, which may receive air discharge from other blowers such as blowers 4300B, 4300C, 4300D respectively. Bulk flow plenum(s) 4380B, 4380C, 4380D may in turn deliver at least some of such air to bulk discharge louvers 4382B, 4382C, 4382D after passing through respective bezels 4381B, 4381C, 4381D.

In an embodiment of the invention, the air treatment system 4000 may comprise bulk discharges 4380B, 4380C, 4380D in a quantity that is equal to the quantity of bulk blowers 4300B, 4300C, 4300C. Bulk discharges 4380B, 4380C, 4380D may be generally aligned with a discharge from a respective blower such as bulk blowers 4300B, 4300C, 4300D, at least in horizontal placement and vertical placement. Thus, air being discharged from a respective bulk blower may continue generally out of the air treatment system 4000, into the vehicle interior space. Each bulk discharge plenum 4380B, 4380C, 4380D may comprise a respective bulk discharge louver 4382B, 4382C, 4382D, which may be a fixed louver. Each bulk discharge may also comprise a bezel 4381B, 4381C, 4381D, which may generally be suitable to conduct flow from the respective bulk blower discharge to the respective bulk discharge louver 4382B, 4382C, 4382D. As illustrated, the bezels 4381B, 4381C, 4381D may provide a small change of angle of the direction of the airflow passing through it, such as a change of angle of less than 30 degrees. Foam gasket 4850 may be in contact with a surface of bezels 4381B, 4381C, 4381D.

As illustrated, for one of the blowers 4300A, the discharge geometry may comprise a directed discharge plenum 4350 that in turn supplies a plurality of directed discharge plenum louvers 4352A, 4352B, 4352C that may be different from the louver(s) that handle the bulk discharge. Directed discharge plenum 4350 may include a bend or other geometric shape. It is possible that air leaving the blower 4300A may pass through one or more bends before reaching the directed discharge louvers 4352A, 4352B, 4352C. Directed discharge louvers 4352A, 4352B, 4352C may branch off of directed discharge plenum 4350, which may also be considered to be a duct, at various places along the duct or directed discharge plenum 4350.

As illustrated, there may be three directed discharge plenum louvers 4352A, 4352B, 4352C and they may be directed in generally different directions from each other in addition to being adjustable. As illustrated, one of the directed discharge plenum louvers 4352A, 4352B, 4352C is directed mostly downward and the other two of the directed discharge plenum louvers 4352A, 4352B, 4352C are directed in a more rearward (with respect to the vehicle) direction. Of course, various combinations and geometries are possible.

The directed discharge plenum louvers 4352A, 4352B, 4352C may be adjustable louvers and may be different from other louvers described herein for this air handling system 4000. In an embodiment, the plurality of directed discharge plenum louvers 4352A, 4352B, 4352C may be adjustable louvers by virtue of having a generally circular exterior that is rotatably mounted in a generally circular mounting. If desired, one degree of adjustability as just described may be provided, or more than one degree of adjustability may be provided.

In an embodiment, the housing of the directed discharge plenum 4350 may extend further toward the occupant region of the vehicle (away from the surface on which the rear of the air treatment system 4000 is mounted), while the other discharge louvers 4382B, 4382C, 4382D may extend to a lesser extent toward the occupant region of the vehicle.

In an embodiment, the air intake 4060 for the air treatment system 4000 may be at a lower elevation than the discharge louvers 4382B, 4382C, 4382D that are associated with the bulk flow plenums 4380B, 4380C, 4380D.

In an embodiment, for the discharges that exit from the bulk discharge plenums 4380A, 4380B, 4380C, the discharge geometry may be at least partially defined by a louver and may additionally comprise, upstream of the bulk discharge louver 4382B, 4382C, 4382D, a directional bezel 4381B, 4381C, 4381D that is at least partially aligned with the louver. The bezels 4381B, 4381C, 4381D may change the direction of the flow by a small angle such as less than 30 degrees. In an embodiment, the bulk discharge louvers 4382B, 4382C, 4382D may be fixed louvers. FIG. 23B shows a bezel 4381, a louver 4382 and a foam gasket 4850.

In an embodiment, as illustrated, the total flow area of the directed discharge louvers 4352A, 4352B, 4352C may be different from the flow area of an individual one of the bulk discharge louvers 4382B, 4382C, 4382D. For example, as illustrated, the total flow area of the three directed discharge louvers 4352A, 4352B, 4352C is less than half of the flow area of one individual bulk discharge louver such as 4382B or 4382C or 4382D. It can be realized that this area relationship affects the total air flowrate through the directed discharge louvers 4352A, 4352B, 4352C, resulting in a larger backpressure in the directed discharge plenum 4350. As a result, the larger velocity of the discharged air through the directed discharge louvers 4352A, 4352B, 4352C, even though the total air flowrate through the various directed discharge louvers 4352A, 4352B, 4352C may be less than the air flowrate through an individual bulk discharge louver such as 4382B or 4382C or 4382D. This increased velocity, in combination with the adjustability of the directed discharge louvers 4352A, 4352B, 4352C, may be advantageous for the comfort of the driver of the vehicle and for the safety of the driver in regard to exposure to microorganisms.

In some situations, it is possible that substantially all of the gas discharged by blower 4300A goes into directed discharge plenum 4350 and thence into directed discharge louvers 4352A, 4352B, 4352C. It is further possible that substantially all of the gas discharged by blower 4300B goes into respective bulk flow plenum 4380B and thence into bulk discharge louver 4382B, and substantially all of the gas discharged by blower 4300C goes into bulk flow plenum 4380C and thence into bulk discharge louver 4382C, and substantially all of the gas discharged by blower 4300D goes into bulk flow plenum 4380D and thence into bulk discharge louver 4382D.

In embodiments, it is possible that the bulk discharge plenum could be separate from the directed discharge plenum 4350, such as by a divider or impervious boundary, rather than being in fluid communication with the directed discharge plenum 4350. In still other embodiments, it is possible that a bulk discharge plenum could be common to less than all of the bulk blowers. In an embodiment, it is possible that there could be dividers such as foam gaskets 4850 such that a bulk discharge plenum 4380B, 4380C, 4380D is uniquely associated with each bulk blower 4300B, 4300C, 4300D, or that each bulk blower 4300B, 4300C, 4300D could be ducted directly to the vehicle interior space without a bulk discharge plenum. Directed discharge plenum 4350 could be kept isolated from the other plenums by a divider such as foam gasket 4850.

In an embodiment of the invention, there are provided two blowers that are mounted on a common shaft of a motor, such that the two blowers 4300A, 4300B on that shaft are constrained to have the same rotational velocity as each other. In the embodiment, the two blowers 4300A, 4300B may be physically identical. However, the load experienced by the two blowers 4300A, 4300B, as described by their respective discharge flow resistances, may be different. It is possible that because the two blowers 4300A, 4300B are physically identical and operate at the same rotational speed as each other, the stagnation pressure that they deliver may be identical. However, due to the differences in downstream flowpath, the flowrates that the respective blowers deliver may be different from each other. In such a situation, the load experienced by the motor 4401 may be influenced by both the fluid delivery situation for Blower 4300A and Blower 4300B. For example, the combination of these situations for the two blowers 4300A and Blower 4300B may be what determines the operating speed and torque of the motor 4401 by which Blower 4300A and Blower 4300B are driven.

It is further possible that the combination of Motor 4401 and Blower 4300A and Blower 4300B may be physically identical to the combination of Motor 4402 and Blower 4300C and Blower 4300D. However, even though the load for three of the blowers (Blower 4300B and Blower 4300C and Blower 4300D) may be generally similar or identical, the load for Blower 4300A may be different. For example, the flowrates through Blower 4300A and Blower 4300V may be different from each other. The load experienced by motor 4402 is a combination of the loads of Blower 4300C and Blower 4300D. Similarly, the load experienced by motor 4401 may be expected to be a combination of the loads of Blower 4300A and Blower 4300B. Thus, the load experienced by motor 4401 and the load experienced by motor 4402 may be different from each other. Thus, the operating rotational speed of Motor 4401 and the operating rotational speed of Motor 4402 might be different from each other, at least in the situation where the electrical power provided to motors 4401, 4402 is identical. This difference may be caused by the uniqueness of directed discharge plenum 4350 and its associated directed discharge louvers 4352A, 4352B, 4352C.

Still further, it is possible that Motor 4401 and Motor 4402 could be powered differently, from their electrical power supply, in order to compensate for the differing load characteristics that the respective motors experience. Such difference in powering characteristics could be provided, for example, by Pulse Width Modulation.

Foam gaskets 4850 for various plenums could be either identical or different from each other. Further, it is possible that some or all of the various foam gaskets 4850 could be combined into a continuous sheet having cutouts in appropriate places.

It can be appreciated that in the described air treatment unit 4000, there is the directed discharge plenum 4350 to discharge through the several directed discharge plenum louvers 4352A, 4352B, 4352C having a combined total discharge area of A1. Furthermore, in combination with this, there is another blower 4300B to bulk discharge louver 4382B having a discharge area of A2, where A2 is larger than A1 by a factor of at least 2, results in the air treatment unit 4000 having the ability to discharge a relatively high-velocity plurality of air jets toward the localized region occupied by the driver, while discharging a broader lower-velocity airflow toward the overall passenger or interior region of the vehicle. In an embodiment, these two objectives can be achieved even while the blower 4300A that is primarily dedicated to the directed discharge plenum is located on the same shaft of the same motor 4401 as a blower 4300B that is primarily dedicated to discharging into a bulk flow plenum such as 4380B. There furthermore may be additional blowers 4300C, 4300D with associated discharge louvers 4382C, 4382D, with associated motor 4402.

In an embodiment, as illustrated in FIG. 22A-22B, the intake grille can extend at least as far in the sideways direction as the array of blowers.

Reference is now made to FIG. 23C, which shows air treatment system 4000 with filter 4100 and certain other parts removed. In an embodiment of the invention, there may be provided a switch 4900 that detects the presence or absence of filter 4100. Switch 4900 may include a lever arm 4910 that bears against filter 4100 if filter 4100 is present and appropriately positioned. Such switch 4900 may be used in the electrical system of air treatment system 4000 to disable certain electrical circuits or functions if filter 4100 is absent or is out of its proper position. A similar switch could be used to disable certain electrical circuits or functions if the overall enclosure or shroud is absent or is out of its proper position.

HEPA-3

Referring now to FIGS. 24-29B, there is shown yet another embodiment of the invention, which may be referred to as HEPA-3. FIG. 24 illustrates an external view of the air treatment unit 3000.

In an embodiment, the air flow pattern through the air treatment unit 3000 may be as illustrated in FIG. 25. The air flow pattern may comprise intake of air from the vehicle interior space by passage of air through a grille 3080, and then passage of the air through a pre-filter 3090, and then passage of that air through a filter 3100 (such as a HEPA filter). The filter 3100 may be contained in a filter housing 3150 that is generally impermeable on sides of the filter housing 3150. The filter housing 3150 may comprise a bent-over retaining edge at the downstream side of the filter 3100, suitable to retain the filter 3100, with there being a corner or corner edge where the retaining edge meets the portion of the filter housing 3150 that surrounds the sides of filter 3100.

There may further be a blower 3300, which may be a centrifugal blower as described elsewhere herein. There may be two blowers 3300 may be powered by a motor 3401.

Air that passes through the filter 3100 (such as a HEPA filter) may then enter an Ultraviolet exposure region 3500 containing a UV light source 3700, and after that the air may then pass through a constriction 3800. Then, the air may enter a blower 3300 and be moved through a louver 3380 and out of the air treatment unit 3000 back into the vehicle interior space. The air treatment unit 3000 may also comprise a shield 3750 that partially defines where ultraviolet light rays emanating from the UV light source 3700 can and cannot propagate to.

In an embodiment, the placement of various internal components may be as illustrated in FIGS. 26-29. FIG. 26 is a slightly angled side view with the shroud and certain components omitted for clarity of illustration. FIG. 27 is a similar view that is a true side view with slightly more components omitted for clarity of illustration, and shown in section to more clearly show the constriction bounded by the shield and the corner edge of the filter housing.

In an embodiment, the constriction 3800 may be elongated in a longitudinal direction. Along this longitudinal direction of the constriction 3800, the boundaries of the constriction 3800 may be defined mostly by two longitudinal edges that may be substantially parallel to each other. One of the longitudinal boundaries of the constriction may be an edge of the shield 3750. The other of the longitudinal boundaries of the constriction 3800 may be a corner edge of the filter housing 3150 in which the HEPA filter 3100 resides. This geometry may be suitable to provide an air treatment unit 3000 that is of compact design utilizing its internal space efficiently. The empty space 3500 near the UV light source 3700 may provide a residence time of air in that UV treatment region 3500, suitably to help kill microorganisms. The constriction 3800 may be one factor in determining the flowrate of air through the air treatment unit 3000. Air may exit through louvers 3380.

FIG. 28 is similar to FIG. 27, but shown in perspective and with the filter 3100, the pre-filter 3090 and the grille 3080 shown exploded apart from each other and from the filter housing 3150. FIG. 29A is a perspective view showing the Ultraviolet exposure region, and the edge of the shield 3750 and the various corner edges of the filter housing 3150. FIG. 29B is another view showing the same components, but viewed more from below and with the base omitted for clarity of illustration.

In an embodiment, the direction of elongation of the constriction 3800 may be parallel to the axis of rotation of the blower(s) 3300. One boundary of the constriction 3800 may be the edge of the shield 3750. Another boundary of the constriction 3800 may be the corner edge of the filter housing 3150. The edge of the shield 3750 and the corner edge of the filter housing 3150 may be generally parallel to each other. Taken together, the edge of the shield 3750 and the corner edge of the filter housing 3150 may make up a majority, or 75% or 80% or 85% of the total perimeter of constriction 3800.

It can be noted that this embodiment could be installed in a vehicle in various ways. For example, the "floor" of the air treatment unit 3000 could be mounted against a ceiling of a vehicle. Alternatively, the "floor" of the air treatment unit 3000 could be mounted against a wall of a vehicle, or against a floor of a vehicle.

Further Embodiments

Embodiments of the invention are further described in the following numbered embodiments.

Regarding HEPA-6:

Embodiment A1. An air treatment system for a vehicle, said vehicle having a forward-rearward direction and a sideways direction and an up-down direction, said directions being mutually orthogonal, said air treatment system being installed at or near a ceiling of said vehicle, said air treatment system comprising:
  an air intake that is oriented in a generally sideways direction;
  a forward air discharge that is located on a forward-facing side of said air treatment system, and is oriented in said forward direction and contains a generally forward-directed louver;
  a rearward air discharge that is located on a rearward-facing side of said air treatment system and is oriented in said rearward direction and contains a generally rearward-directed louver; and
  a downward air discharge that is located on a downward-facing side of said air treatment system and is oriented in said downward direction and contains a generally downward-directed louver,
  wherein said forward-directed louver comprises an upper vane that extends generally side-to-side and is generally forward-directed, and comprises a lower vane that extends generally side-to-side and is forward-directed, said upper forward-directed vane being closer to said ceiling than said lower forward-directed vane, said lower forward-directed vane pointing more downward than said upper forward-directed vane,
  wherein said rearward-directed louver comprises an upper vane that extends generally side-to-side and is rearward-directed, and comprises a lower vane that extends generally side-to-side and is generally rearward-directed, said upper rearward-directed vane being closer to said ceiling than said lower rearward-directed vane, said lower rearward-directed vane pointing more downward than said upper rearward-directed vane, and
  wherein said downward-directed louver comprises a downward-directed-louver first-side vane that extends in a generally forward-rearward direction and is generally downward-directed, and comprises a downward-directed louver second-side vane that extends generally forward-rearward and is generally downward-directed, one of said vanes being vertical or closer to vertical, and the other of said vanes being less close to vertical, wherein said vanes that are vertical or closer to vertical are located, in said sideways direction, further away from said intake, and wherein said vanes that are less close to vertical are located closer to said intake.

Embodiment A2. The system of Embodiment A1, wherein said upper forward-directed vane points generally horizontally, and wherein said upper rearward-directed vane points generally horizontally.

Embodiment A3. The system of Embodiment A1, wherein said downward-directed-louver first-side vane points generally vertically downward and said downward-directed louver second-side vane is angled to direct flow toward a center of said vehicle.

Embodiment A4. The system of Embodiment A1, wherein said system comprises a plurality of said downward-directed louvers aligned in a linear manner with each other.

Embodiment A5. The system of Embodiment A1, wherein said forward-directed louver and said rearward-directed louver and said downward-directed louver all have respective outline shapes that are elongated rounded-rectangular having respective elongated directions, and wherein said forward-directed louver and said rearward-directed louver have their elongated directions along said sideways direction of said vehicle, and wherein a plurality of said downward-directed louver are spaced in a linear arrangement along said forward-backward direction of said vehicle and have their elongated directions along said forward-backward direction of said vehicle.

Embodiment A6. The system of Embodiment A1, wherein said system comprises said forward-directed louver and said rearward-directed louver and comprises a plurality of said downward-directed louvers, and wherein all of said louvers are substantially identical to each other.

Embodiment A7. The system of Embodiment A1, wherein said system comprises a quantity of said downward-directed louver that equals a quantity of blowers in said system, said blowers discharging into a common plenum from which all of said louvers emanate.

Embodiment A8. The system of Embodiment A1, wherein one of said air treatment system is provided near a front of said vehicle and another of said of said air treatment system is provided near a rear of said vehicle, said air treatment systems being located on opposite sides of a central aisle of said vehicle.

Embodiment A9. The system of Embodiment A1, wherein said vehicle has an interior volume, and said system, or a plurality of said systems installed in said vehicle, is able to provide between 12 and 24 changes of said interior volume per hour.

Embodiment A10. The system of Embodiment A1, further comprising, along a flow direction, the following components: a grille, followed by a pre-filter, followed by a HEPA filter, followed by a blower, followed by a plenum that discharges through said louvers.

Embodiment A11. The system of Embodiment A1, further comprising, along a flow direction, the following components: a grille, followed by a pre-filter, followed by a HEPA filter, followed by a region of exposure to UV light, followed by a blower, followed by a plenum that discharges through said louvers.

Embodiment A12. The system of Embodiment A1, wherein said system comprises a HEPA filter and a blower and a shield and a source of UV light, and wherein at least some of a surface of said HEPA filter is exposed to said UV light, and wherein said shield is located so as to block an intake region of said blower from direct UV light.

Embodiment A13. The system of Embodiment A1, wherein said system comprises a source of UV light that has a tubular shape elongated in an elongation direction, and comprises a shield that is elongated along said elongation direction, and said shield is longer than a length of said tubular UV light source.

Embodiment A14. The system of Embodiment A1, wherein said system comprises a UV light source that has a tubular shape elongated in an elongation direction, and comprises a shield that is elongated along said elongation direction, and said shield is longer than a distance from an extreme end of one extreme blower to an extreme end of an extreme blower in an opposite direction along a direction parallel to an elongate direction of said UV light source.

Embodiment A15. The system of Embodiment A1, wherein said system comprises a filter that is able to capture 99.99% of particles having a size of 0.3 microns at a face velocity of 100 feet per minute.

Embodiment A16. The system of Embodiment A1, wherein said system further comprises a cooling coil or heat transfer coil or an evaporator or a humidity control device.

Embodiment A17. The system of Embodiment A1, wherein a duration of exposure of air to UV as the air passes through the air treatment region in a single pass through the air treatment system is several seconds.

Embodiment A18. The system of Embodiment A1, further comprising a UV light source and a shield and a centrifugal blower having a blower intake, wherein said blower intake is in a shadow of said shield with respect to said ultraviolet light source.

Embodiment A19. The system of Embodiment A1, further comprising a centrifugal blower having a blower intake and an axis of rotation, wherein said blower intake is directed along an axis of rotation of said blower.

Embodiment A20. The system of Embodiment A1, wherein said vehicle is a van, a recreational vehicle, a small bus, a school bus, a transit bus, a shuttle bus, a paratransit vehicle, an ambulance, an emergency vehicle, or a vehicle with a rated capacity of 7 to 50 people.

Regarding HEPA-4:

Embodiment B1. An air treatment system for a vehicle, said air treatment system comprising:
  an air intake containing therein a filter;
  an air treatment region comprising therein a UV light source suitable to direct UV light from said UV light source at air passing through said air treatment region;
  a directed discharge blower and a bulk discharge blower, each of said blowers taking in air that has passed through said filter and said air treatment region, each of said blowers having a respective blower discharge;
  a directed discharge plenum, capable of receiving discharge from said directed discharge blower, said directed discharge plenum having, emanating therefrom, a plurality of directed discharge louvers at least some of which are not aligned with or are offset from said discharge of said first blower; and
  a bulk flow plenum, capable of receiving discharge from said bulk discharge blower, said bulk flow plenum having a bulk flow plenum exit louver,
  wherein said directed discharge blower and said bulk discharge blower are both driven by a first motor.

Embodiment B2. The system of Embodiment B1, wherein said directed discharge blower and said bulk discharge blower are physically identical to each other.

Embodiment B3. The system of Embodiment B1, wherein said directed discharge blower and said bulk discharge blower share a common axis of rotation.

Embodiment B4. The system of Embodiment B1, wherein said directed discharge louvers are located suitably to be directed at a driver of said vehicle when said system is located at a front of said vehicle.

Embodiment B5. The system of Embodiment B1, wherein said directed discharge louvers are adjustable in either their area, or their direction in which they direct air passing therethrough, or both.

Embodiment B6. The system of Embodiment B1, wherein said directed discharge louvers comprise at least one of said directed discharge louvers that discharges through a surface that is mostly downward-facing and at least one other of said directed discharge plenum louvers that discharges through a surface that is mostly rearward-facing with respect to said vehicle.

Embodiment B7. The system of Embodiment B1, wherein a total discharge area of said directed discharge louvers is less than half of a discharge louver area of said bulk flow plenum exit louver.

Embodiment B8. The system of claim 1, wherein an intake grille area is greater than a total louver area of all discharge louvers in said air treatment system.

Embodiment B9. The system of Embodiment B1, wherein said filter is a HEPA filter.

Embodiment B10. The system of claim 1, wherein at least some of a surface of said filter is exposed to said UV light.

Embodiment B11. The system of Embodiment B1, wherein said directed discharge plenum and said bulk discharge plenum are separated from each other by a gasket or a seal or a foam divider that generally prevents intermixing of flow between said directed discharge plenum and said bulk discharge plenum.

Embodiment B12. The system of Embodiment B1, further comprising a second bulk discharge blower and a third bulk discharge blower, said second bulk discharge blower and said third bulk discharge blower being driven by a second motor.

Embodiment B13. The system of Embodiment B12, wherein said directed discharge blower and said first bulk discharge blower said second bulk discharge blower and said third bulk discharge blower are identical to each other and said first motor and said second motor are identical to each other, but said first motor and said second motor are electrically powered in different manners.

Embodiment B14. The system of Embodiment B1, wherein said directed discharge plenum extends further laterally than said air intake extends laterally.

Embodiment B15. The system of Embodiment B1, further comprising a switch to detect a presence of said filter and to disable at least some operation of said system if said filter is missing or incorrectly positioned.

Regarding HEPA-3:

Embodiment C1. An air treatment system for a vehicle, said air treatment system comprising:
  an air intake in fluid communication with a vehicle interior space;
  a filter downstream of said air intake, said filter being housed in a filter housing that is generally impermeable through surfaces of said filter housing;
  an ultraviolet exposure region downstream of said filter, said ultraviolet exposure region comprising an Ultraviolet light source;
  a shield, said shield being suitable to block propagation of UV light rays from said Ultraviolet light source in certain directions; and
  an air moving device, suitable to move air from said air intake to a discharge,
  wherein a flowpath from said intake to said discharge comprises, in sequence, said intake, and said filter, and said ultraviolet exposure region, and a constriction, and said air moving device, and said discharge, wherein said shield has a shield longitudinal edge extending in a longitudinal direction and said filter housing has an external corner edge extending along said longitudinal direction, wherein said constriction in said flowpath of air from said inlet to said discharge is formed at least in part by said shield longitudinal edge and said filter housing external corner edge.

Embodiment C2. The system of Embodiment C1, wherein said shield longitudinal edge and said filter housing external corner edge are substantially parallel to each other.

Embodiment C3. The system of Embodiment C1, wherein, in combination, said shield longitudinal edge and said filter housing external corner edge make up more than 50% of a perimeter of said constriction.

Embodiment C4. The system of Embodiment C1, wherein said constriction has a flow area that is less than a cross-sectional flow area of said filter.

Embodiment C5. The system of Embodiment C1, wherein said shield longitudinal edge is approximately in a projection of an external plane of said filter housing.

Embodiment C6. The system of Embodiment C1, wherein said UV light source is a tubular bulb having a bulb axis parallel to said longitudinal direction.

Embodiment C7. The system of Embodiment C1, wherein said air moving device is a centrifugal blower having an axis of rotation, and said axis of rotation is parallel to said longitudinal direction.

Embodiment C8. The system of Embodiment C1, further comprising a pre-filter upstream of said filter and a grille upstream of said pre-filter.

Embodiment C9. The system of Embodiment C1, wherein said filter is a HEPA filter.

Further Remarks

It is believed that embodiments of the invention are highly effective in removing or killing pathogens such as viruses from interior spaces of vehicles.

In general, embodiments of the invention may contain ultraviolet sources that emit ultraviolet light at any wavelength or combination of wavelengths such as to be effective for disinfecting or killing a desired pathogen. Furthermore, emission of UV light may be performed in any sequence that may be effective for killing or inactivating a pathogen of interest.

A UV light source can be a conventional plasma-containing tubular bulb, or can be a Light Emitting Diode, or can be any other source or combination thereof.

The term "air" can be understood to mean not only air, but also any gas in general.

Air treatment units as described may be installed at or near the ceiling of the vehicle but alternatively may be installed in other locations such as along the wall or on the floor, in any desired orientation, especially for HEPA-3.

Any described type of louver could be used in any situation. For example, a louver with two different angles of vanes could be used even if not so described, or a louver with all parallel vanes could be used even if not so described. A louver having two different directions of vanes could, as described, have one of the directions aligned with the louver axis and the other direction not aligned with the louver axis. Alternatively, such a louver could have two different directions of vanes with neither of the vane directions being aligned with the louver axis.

Filters can include reinforcing structure to help support the filtration medium, as appropriate for the dimensions and proportions of the filter and the pressure drop across the filter during operation.

It is further possible that a component of the apparatus could contain a photocatalytic agent such as titanium dioxide.

It is further possible to use ozone as a disinfectant, as described herein. Ozone could be created by UV light if the wavelength of the UV light is appropriate, or it could be created by other means. Such use of ozone could be performed in conjunction with any of the other means described herein, in any combination.

Any embodiment may be equipped with an interlock or switch or microswitch to detect the presence or absence of a component such as a filter or a shroud. The absence or mispositioning of such component may result in disabling some or all functions of the system, or supply of power to some or all components of the system.

Terms such as generally forward, generally rearward and generally downward are intended to mean within 15 degrees of true forward or rearward or downward.

Embodiments of the invention can be used in generally any vehicle, including vans, recreational vehicles, small buses, school buses, transit buses, shuttle buses, paratransit vehicles, ambulances, emergency vehicles, and other types of vehicles having a rated capacity of 7 to 50 people. Embodiments of the invention could also be used in non-vehicular applications.

It is also possible that a cooling coil or evaporator or heat transfer coil or heater, or humidity controller or moisture absorber could be included in the apparatus, thereby also providing a heat exchange or temperature control or humidity control function.

Although it has been described that discharges from various blowers may be separated from discharges from other blowers by separators such as foam gaskets, it is possible that such separation need not be perfect and some cross-flow between plenums may be allowed or provided.

An air moving device could be a centrifugal blower as described, but could alternatively be a fan or generally any type of air moving device.

In general, any combination of disclosed features, components and methods described herein is possible. Features described for one embodiment can be used in other embodiments. Steps of a method can be performed in any order that is physically possible.

All cited references are incorporated by reference herein.

Although embodiments have been disclosed, it is not desired to be limited thereby. Rather, the scope should be determined only by the appended claims.

We claim:

1. An air treatment system for a vehicle, said vehicle having a forward-rearward direction and a sideways direction and an up-down direction, said directions being mutually orthogonal, said air treatment system being installed at or near a ceiling of said vehicle, said air treatment system comprising:

an air intake that is oriented in a generally sideways direction;

a forward air discharge that is located on a forward-facing side of said air treatment system, and is oriented in a forward direction and contains a generally forward-directed louver;

a rearward air discharge that is located on a rearward-facing side of said air treatment system and is oriented in a rearward direction and contains a generally rearward-directed louver; and a downward air discharge that is located on a downward-facing side of said air treatment system and is oriented in a downward direction and contains a generally downward-directed louver, wherein said forward-directed louver comprises an upper vane that extends generally side-to-side and is generally forward-directed, and comprises a lower vane that extends generally side-to-side and is generally forward-directed, said upper forward-directed vane being closer to said ceiling than said lower forward-directed vane, said upper forward-directed vane having an upper forward-directed vane angle with respect to a horizontal plane, measured with respect to an axis that extends in said sideways direction, said lower forward-directed vane having a lower forward-directed vane angle with respect to said horizontal plane, measured with respect to said axis that extends in said sideways direction, said lower forward-directed vane angle being greater than said upper forward-directed vane angle, wherein said rearward-directed louver comprises an upper vane that extends generally side-to-side and is generally rearward-directed, and comprises a lower vane that extends generally side-to-side and is generally rearward-directed, said upper rearward-directed vane being closer to said ceiling than said lower rearward-directed vane, said upper rearward-directed vane having an upper rearward-directed vane angle with respect to said horizontal plane, measured with respect to an axis that extends in said sideways direction, said lower rearward-directed vane having a lower rearward-directed vane angle with respect to said horizontal plane, measured with respect to said axis that extends in said sideways direction, said lower rearward-directed vane angle being greater than said upper rearward-directed vane angle, wherein said downward-directed louver comprises a downward-directed-louver first-side vane that extends in a generally forward-rearward direction and is generally downward-directed, and comprises a downward-directed louver second-side vane that extends generally forward-rearward and is generally downward-directed, said downward-directed-louver second-side vane being located closer to said intake than said downward-directed-louver first-side vane, said downward-directed-louver first-side vane having a first downward-directed vane angle with respect to a vertical plane, measured with respect to an axis that extends in said forward-rearward direction, said downward-directed louver second-side vane having a second downward-directed vane angle with respect to said vertical plane, measured with respect to said axis that extends in said forward-rearward direction, said second downward-directed vane angle being greater than said first downward-directed vane angle, and wherein said air treatment system comprises a HEPA filter and a blower and a shield and a source of UV light, and wherein at least some of a surface of said HEPA filter is exposed to said UV light, and wherein said shield is located so as to block an intake region of said blower from direct UV light.

2. The air treatment system of claim 1, wherein said upper forward-directed vane points generally horizontally, and wherein said upper rearward-directed vane points generally horizontally.

3. The air treatment system of claim 1, wherein said downward-directed-louver first-side vane points generally vertically downward and said downward-directed louver second-side vane is angled to direct flow toward a center of said vehicle.

4. The air treatment system of claim 1, further comprising, along a flow direction, the following components: a grille, followed by a pre-filter, followed by said HEPA filter, followed by a region of exposure to said UV light, followed by said blower, followed by a plenum that discharges through at least one of said forward air discharge, said rearward air discharge and said downward air discharge.

5. The air treatment system of claim 1, wherein said source of UV light has a tubular shape elongated in an elongation direction, and said shield is elongated along said elongation direction, and said shield is longer than a length of said tubular UV light source.

6. The air treatment system of claim 1, wherein said blower is a centrifugal blower.

7. The air treatment system of claim 1, wherein said vehicle is selected from the group consisting of a van, a recreational vehicle, a small bus, a school bus, a transit bus, a shuttle bus, a paratransit vehicle, an ambulance, an emergency vehicle, or a vehicle with a rated capacity of 7 to 50 people.

* * * * *